(12) United States Patent
Gatenby et al.

(10) Patent No.: US 7,700,328 B2
(45) Date of Patent: Apr. 20, 2010

(54) METHOD FOR PRODUCING AN L-TYROSINE OVER-PRODUCING BACTERIAL STRAIN

(75) Inventors: Anthony A. Gatenby, Wilmington, DE (US); Ranjan Patnaik, Newark, DE (US); Fateme Sima Sariaslani, Wilmington, DE (US); Wonchul Suh, Hockessin, DE (US); Tina K. Van Dyk, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 352 days.

(21) Appl. No.: 11/448,331

(22) Filed: Jun. 7, 2006

(65) Prior Publication Data

US 2008/0118958 A1    May 22, 2008

(51) Int. Cl.
*C12P 13/22* (2006.01)
*C12P 21/06* (2006.01)
*C12P 19/34* (2006.01)
*C12N 15/87* (2006.01)
*C12N 15/74* (2006.01)
*C12N 15/00* (2006.01)

(52) U.S. Cl. .................. 435/108; 435/463; 435/252.33; 435/471; 435/488; 435/477; 435/69.1; 435/91.1; 435/320.1

(58) Field of Classification Search ........................ None
See application file for complete search history.

(56) References Cited

U.S. PATENT DOCUMENTS

| | | | |
|---|---|---|---|
| 2,973,304 A * | 2/1961 | Huang | 435/108 |
| 4,681,852 A * | 7/1987 | Tribe | 435/108 |
| 6,368,837 B1 | 4/2002 | Gatenby et al. | |
| 2004/0001860 A1 | 1/2004 | Cheung | |
| 2004/0248267 A1 | 12/2004 | Ben Bassat et al. | |
| 2005/0148054 A1 | 7/2005 | Qi et al. | |
| 2005/0277179 A1 * | 12/2005 | Takai et al. | 435/108 |

FOREIGN PATENT DOCUMENTS

| | | |
|---|---|---|
| EP | 0 263 515 A2 | 4/1988 |
| EP | 0 332 234 B1 | 9/1989 |
| EP | 1616940 A1 | 1/2006 |

OTHER PUBLICATIONS

Sousa et al., The ARO4 gene of *Candida albicans* encodes a tyrosine-sensitive DAHP synthase: evolution, functional conservation and phenotype of Aro3p-, Aro4p-deficient mutants. Microbiology, 2002, vol. 148: 1291-1303.*
Whisstock et al., Prediction of protein function from protein sequence. Q. Rev. Biophysics., 2003, vol. 36 (3): 307-340.*
Camakaris et al. Regulation of tyrosine and phenylalanine biosynthesis in *Escherichia coli* K-12: properties of the tyR gene product. J. Bacteriol., 1973, vol. 115, No. 3: 1135-1144.*
P.A. Kumar et. al., Synthesis and Characterization of a Novel Ferroelectric Liquid Crystal Compound Derived From L-Tyrosine, Z. Naturforsch., 2002, vol. 57:803-806.
Maiti et. al., Microbial Production of L-Tyrosine: A Review, Hindustan Antibiot. Bull., 1995, vol. 37:51-65.
Ikeda et. al., Metabolic Engineering to Produce Tyrosine or Phenylalanine in a Tryptophan-Producing *Corynebacterium glutamicum* Strain, Appl. Environ. Microbiol., 1992, vol. 58:781-785.
Gerhard H. Braus, Aromatic Amino Acid Biosynthesis in the Yeast *Saccharomyces cerevisiae*: A Model System for the Regulation of a Eukaryotic Biosynthetic Pathway, Microbiological Reviews, 1991, vol. 55:349-370.
Olson, Monica M. et al., Production of tyrosine from sucrose or glucose achieved by rapid genetic changes to phenylalanine-producing *Escherichia coli* strains, Applied Microbiology and Biotechnology, 2007, p. 1031-1040, vol. 74, No. 5.

* cited by examiner

*Primary Examiner*—Ganapathirama Raghu

(57) ABSTRACT

An enteric bacterial strain was engineered to over-produce L-tyrosine using a one-step method. The pheA-tyrA chromosomal region of the bacterial genome was replaced with an engineered chromosomal segment, resulting in inactivation of the pheA coding region and strong expression of the tyrA coding region, resulting in high levels of L-tyrosine production.

9 Claims, 6 Drawing Sheets

METHOD FOR PRODUCING AN L-TYROSINE OVER-PRODUCING BACTERIAL STRAIN

FIELD OF THE INVENTION

The invention relates to the field of molecular biology and microbiology. More specifically, the invention relates to methods of engineering bacterial hosts in one step to produce strains that over-produce L-tyrosine.

BACKGROUND OF THE INVENTION

Production of chemicals from microorganisms has been an important application of biotechnology. Tyrosine is an attractive chemical for production in microorganisms due to its nutritional and pharmaceutical uses, such as being a dietary supplement and a reagent for production of the anti-Parkinson's drug, L-DOPA. In addition, tyrosine has potential as a reagent for the production of other chemicals with valuable industrial applications. Compounds that may potentially be made from tyrosine include (S)-4-(2-chloro-3-(4-n-dodecyloxy)-phenylpropionato)-4'4(2-methyl)butyloxy-biphenylcarboxylate (CDPMBB; Kumar and Pisipati (Z. Naturforsch. 57a:803-806 (2002)), p-hydroxycinnamic (pHCA; U.S. Pat. No. 6,368,837, US20050148054A1), p-hydroxystyrene (pHS; also know as p-vinylphenol; US2004001860), and acetylated derivatives thereof, such as p-acetoxystyrene (also known as ASM). CDPMBB is a ferroelectric material for use in ferroelectric liquid crystals (FLC). PHCA is a useful monomer for production of Liquid Crystal Polymers (LCP). LCPs may be used in electronic connectors and telecommunication and aerospace applications. LCP resistance to sterilizing radiation has also enabled these materials to be used in medical devices as well as chemical, and food packaging applications. Hydroxystyrenes have application as monomers for the production of resins, elastomers, adhesives, coatings, automotive finishes, inks and photoresists, as well as in electronic materials. They may also be used as additives in elastomer and resin formulations.

Tyrosine is made naturally in microorganisms, but is generally present at low levels that are sufficient for cellular growth. The tyrosine biosynthetic pathway branches from the phenylalanine biosynthetic pathway with the chorismate mutase/prephenate dehydrogenase enzyme, encoded by tyrA in E. coli, acting on the chorismate substrate. In the phenylalanine pathway chorismate is the substrate of chorismate mutase/prephenate dehydratase, which is encoded by the pheA gene in E. coli.

Microorganisms with increased levels of tyrosine production have been obtained through traditional genetic methods as well as through genetic engineering. Expression of either pheA, or the genes encoding chorismate mutase/prephenate dehydratase in other organisms, has been reduced or eliminated, thereby reducing or eliminating competition for the chorismate substrate by chorismate mutase/prephenate dehydratase, resulting in increased tyrosine production [Maiti et al. (1995) Microbial production of L-tyrosine: a review. Hindustan Antibiot. Bull. 37:51-65].

Separately, either tyrA expression or the genes encoding chorismate mutase/prephenate dehydrogenase in other organisms has been increased thereby increasing the cellular capacity to direct chorismate toward tyrosine production, with increased chorismate mutase/prephenate dehydrogenase enzyme activity. EP 0332234 discloses a process for producing tyrosine in a Corynebacterium or Brevibacterium host by transforming with a plasmid carrying genes encoding 3-deoxy-2-keto-D-arabino-heptulosonate-7phosphate (DAHP) synthase (first enzyme of the aromatic amino acid biosynthetic pathway), chorismate mutase, and prephenate dehydrogenase. EP 0263515 discloses a process for producing tyrosine in a Corynebacterium or Brevibacterium host that produces tryptophan. The tryptophan producing Corynebacterium or Brevibacterium host is transformed with a plasmid carrying genes encoding DAHP synthase and chorismate mutase.

Commonly owned US20040248267 discloses engineering of a tyrosine excreting E. coli strain by first introducing a mutant pheA gene. Then in a second separate step, a trc promoter driven tyrA gene was introduced. Rare transductants having both introductions were identified as tyrosine excreting strains.

In addition, commonly owned US 20050148054 A1 discloses increasing tyrosine production by expressing phenylalanine hydroxylase in a recombinant organism to convert phenylalanine to tyrosine.

In spite of the efforts to engineer microorganisms for the production of tyrosine the highest reported level is only 26 g/l for Corynebacterium glutamicum (Ikeda, M. and R. Katsumata. 1992. Appl. Environ. Microbiol. 58: 781-785). There remains a need therefore for microorganisms that produce L-tyrosine in higher levels to facilitate the commercial production of tyrosine. Applicants have solved the stated problem by engineering a recombinant enteric bacteria to produces L-tyrosine at levels in excess of 26 g/l.

SUMMARY OF THE INVENTION

The invention relates to tyrosine over-producing strains and methods of making the same. The strains of the invention comprise disruptions in the pheA gene to render it non-functional, and up-regulation or over-expression of tyrA using a single insertion method for genetic insertions. The strains may additionally comprise other modulations of the aromatic amino acid pathway and other phenotypic traits that enhance the utility of the strain for the production of tyrosine.

Accordingly the invention provides a method for making an L-tyrosine over-producing bacterial strain comprising:
  a) providing an enteric bacterial strain comprising:
    i) an endogenous pheA-tyrA chromosomal region; and
    ii) an aromatic amino acid biosynthetic pathway that produces chorismate;
  b) inserting into the chromosome of the strain of step (a) an engineered chromosomal segment comprising:
    1) a nucleic acid fragment comprising a promoter operably linked to an open reading frame encoding tyrA; and
    2) a non-functional pheA nucleic acid sequence;
  wherein the engineered chromosomal segment replaces the endogenous pheA-tyrA region of the host chromosome creating an L-tyrosine over-producing strain.

In a preferred embodiment the invention provides a tyrosine over-producing strain made by the methods of the invention. Alternatively the invention provides a tyrosine overproducing enteric bacterial strain comprising the following characteristics:
  a) the presence of an aromatic amino acid biosynthetic pathway comprising genes selected from the group consisting of aroF, aroG, aroH, aroB, aroD, aroE, aroL, aroK, aroA, aroC, tyrA, pheA and tyrB
  b) a non-functional pheA gene///
  c) overexpression of the tyrA gene under the control of a promoter selected from the group consisting of lac, ara, tet, trp, lambda $P_L$, lambda $P_R$, T7, tac, trc, malE, T3, T4, T5, rrnB, lpp, phoA, proU, cst-1, cadA, nar, cspA, gyrA, Bacillus spp nprM, and Streptomyces spp glucose isomerase;

d) resistance to 3-fluorotyrosine;
e) resistance to para-fluorophenylalanine;
f) resistance to β-2-thienylalanine;
g) resistance to tyrosine; and
h) resistance to high phenylalanine and high temperature.

In another embodiment the invention provides a method for producing L-tyrosine comprising:
a) providing tyrosine overproducing enteric bacterial strain made by the methods of the invention; and
b) growing said tyrosine over-producing strain under conditions where L-tyrosine is produced.

BRIEF DESCRIPTION OF THE DRAWINGS AND SEQUENCE DESCRIPTIONS

The invention can be more fully understood from the following detailed description, the figures, and the accompanying sequence descriptions that form a part of this application.

FIG. 1 is an illustration of the aromatic amino acid biosynthetic pathway

FIG. 2 A) shows a diagram of coding regions in and surrounding the pheA-tyrA region in the *E. coli* chromosome, and the region targeted for deletion (Δ), with the primer homology regions (A and B). B) shows a diagram of the PCR template tetA and tetR gene region, and primers used in two PCR reactions to produce DNA fragments for TetRA circle formation.

Figure 1:
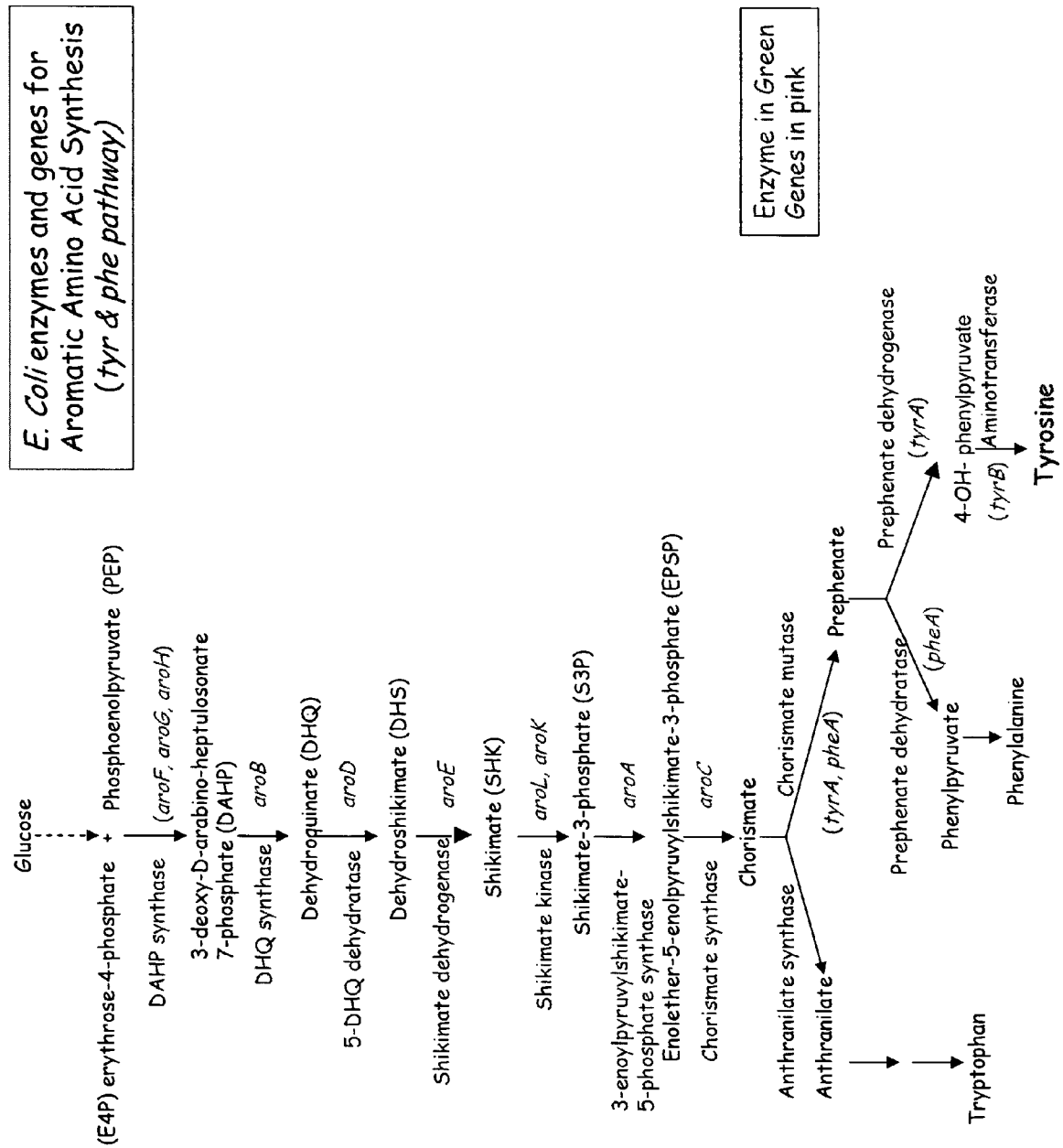

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 CFR 1.52(e). The Compact Discs are submitted in duplicate and are identical to one another. The discs are labeled "Copy 1—Sequence Listing" and "Copy 2 Sequence listing" The discs contain the following file: CL3305 seq list.ST25 having the following size: 40,000 bytes and which was created May 12, 2006.

SEQ ID NO:1 is a nucleotide sequence of the pheA-tyrA region of *E. coli* K12.

SEQ ID NO:2 is a nucleotide sequence of the pheA-tyrA region of *E. coli* O157:H7.

SEQ ID NO:3 is a nucleotide sequence of the pheA-tyrA region of *E. coli* CFT073.

SEQ ID NO:4 is a nucleotide sequence encoding PheA of *E. coli* K12.

SEQ ID NO:5 is a nucleotide sequence encoding PheA of *E. coli* O157:H7.

SEQ ID NO:6 is a nucleotide sequence encoding PheA of *E. coli* CFT073.

SEQ ID NO:7 is a nucleotide sequence encoding TyrA of *E. coli* K12.

SEQ ID NO:8 is a nucleotide sequence encoding TyrA of *E. coli* O157:H7.

SEQ ID NO:9 is a nucleotide sequence encoding TyrA of *E. coli* O157:H7.

SEQ ID NO:10 is the amino acid sequence of *Yersinia pestis biovar Medievalis* str. 91001 PheA protein.

SEQ ID NO:11 is the amino acid sequence of *E. coli* K12 PheA protein.

SEQ ID NO:12 is the amino acid sequence of *Erwinia carotovora* subsp. *atroseptica* SCRI1043PheA protein.

SEQ ID NO:13 is a nucleotide sequence encoding TyrA of *Salmonella typhimurium* LT2.

SEQ ID NO:14 is a nucleotide sequence encoding TyrA of *Photorhabdus luminescens* subsp. *laumondii* TTO1.

SEQ ID NO:15 is a nucleotide sequence encoding TyrA of *Shewanella oneidensis* MR-1.

SEQ ID NO:16 is a nucleotide sequence encoding TyrA of *Xanthomonas campestris* pv. campestris str. ATCC 33913.

SEQ ID NO:17 is the nucleotide sequence of primer ABTR.

SEQ ID NO:18 is the nucleotide sequence of primer BATA.
SEQ ID NO:19 is the nucleotide sequence of primer TR.
SEQ ID NO:20 is the nucleotide sequence of primer TA.
SEQ ID NO:21 is the nucleotide sequence of primer T-kan (tyrA).
SEQ ID NO:22 is the nucleotide sequence of primer B-kan (trc).
SEQ ID NO:23 is the nucleotide sequence of primer T-trc (kan).
SEQ ID NO:24 is the nucleotide sequence of primer B-trc (tyrA).
SEQ ID NO:25 is the nucleotide sequence of primer T-ty (test).
SEQ ID NO:26 is the nucleotide sequence of primer B-ty (test).
SEQ ID NO:27 is the nucleotide sequence of primer Lac__1.
SEQ ID NO:28 is the nucleotide sequence of primer Lac__2.
SEQ ID NO:29 is the nucleotide sequence of primer Lac__3.
SEQ ID NO:30 is the nucleotide sequence of primer Lac__4.
SEQ ID NO:31 is the nucleotide sequence of the *E. coli* K12 tyrR gene.

DETAILED DESCRIPTION

The present invention describes methods for engineering a tyrosine overproducing strain in an enteric bacterial host which has a pheA-tyrA chromosomal region and the aromatic amino acid biosynthetic pathway at least through the chorismate product. In a one-step process the pheA coding region of the pheA-tyrA chromosomal region is inactivated and a chimeric gene including a strong promoter and a tyrA coding region is inserted in the chromosome. The strong expression of tyrA in the absence of pheA expression converts the host strain to one producing high levels of tyrosine, also called over-production, such that tyrosine is excreted from the cells.

In this disclosure, a number of terms and abbreviations are used. The following definitions are provided.

"Polymerase chain reaction" is abbreviated PCR.
"Ampicillin" is abbreviated amp.
"Kanamycin is abbreviated kan.

The term "invention" or "present invention" as used herein is meant to apply generally to all embodiments of the invention as described in the claims as presented or as later amended and supplemented, or in the specification.

"Gene" refers to a nucleic acid fragment that expresses a specific protein, including regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. The term "open reading frame" refers to that portion of a gene or genetic construct the encodes a polypeptide but may be devoid of any regulatory elements. The term "genetic construct" will refer to any combination of genetic elements, including without limitation, genes, regulatory elements, open reading frames and the like assembled within a single nucleic acid sequence and capable of effecting a particular genetic or phenotic trait when transformed into an appropriate host.

The term "deletion" or "disruption" when used in reference to a gene, genetic construct or the like with refer to the partial or complete inactivation of nucleic acid sequence as it normally functions. A deletion in a sequence means the removal of all or part of the sequence which may results in the complete or partial inactivation of the sequence. A disruption or insertion in the sequence will refer the addition of an element within the sequence that will again decrease or eliminate the ability of the sequence to function normally. Deletions, or disruptions will render the gene or coding sequence "non-functional" within the meaning the present invention.

"Coding sequence" or "coding region" refers to a DNA sequence that codes for a specific amino acid sequence.

"Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

The term "overexpression" refers to the production of a gene product in transgenic organisms that exceeds levels of production in normal or non-transformed organisms.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that is not translated yet has an effect on cellular processes.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", and "vector" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

"pheA" refers to a gene found in an enteric bacteria encoding chorismate mutase/prephenate dehydratase and PheA refers to the corresponding encoded protein.

"tyrA" refers a gene found in enteric bacteria encoding chorismate mutase/prephenate dehydrogenase, and TyrA refers to the corresponding encoded protein.

"tyrR" refers a gene found in enteric bacteria that regulates the expression of various elements of the aromatic amino acid biosynthetic pathway including the gene products of the aroF, tyrA, aroG, aroL, and tyrB genes.

"PEP" is the abbreviation for Phosphoenolpyruvate

"DAHP" is the abbreviation for 3-deoxy-D-arabino-heptulosonate 7-phosphate

"DHQ" is the abbreviation for Dehydroquinate

"DHS" is the abbreviation for Dehydroshikimate

"SHK" is the abbreviation for Shikimate

"S-3P" is the abbreviation for shikimate-3-phosphate.

"ESPS is the abbreviation for Enolether-5-enolpyruvylshikimate-3-phosphate.

"CHA" is the abbreviation for chorismate.

"PPA" is the abbreviation for prephenate

"HPP" is the abbreviation for 4-OH— phenylpyruvate

"Tyr" is the abbreviation for tyrosine

"Phe" is the abbreviation for phenylalanine.

The term "aroG397" refers to a specific mutation in the aroG gene that results in the production of a DAHP synthase enzyme that is resistant to feed back inhibition by phenylalanine. The aroG397 mutation is common and well known in the art and is documented in U.S. Pat. No. 4,681,852, incorporated herein by reference.

As used herein the term "tyrR366 mutation" has the effect of inactivating, down regulating, or making non-functional the tyrR gene. Within the context of the present methods for the production of tyrosine, down regulation of tyrR results in the upregulation of a number of the enzymes of the aromatic biosynthetic pathway for which TyrR represses expression. The tyrR366 mutation is well known in the art and is well documented in [Camakaris and Pittard (1973) J. Bacteriol. 115: 1135-1144].

The term "aromatic amino acid biosynthetic pathway" refers to a ubiquitous enzymatic pathway found in many microorganisms responsible for phenylalanine and tyrosine production. As used herein the aromatic amino acid biosynthetic pathway is illustrated in FIG. 1 and, in part, comprises the enzymes encoded by the genes aroF, aroG, aroH, aroB, aroD, aroE, aroL, aroK, aroA, aroC, tyrA, pheA and tyrB The term "phenylalanine over-producing strain" refers to a microbial strain that produces endogenous levels of phenylalanine that are significantly higher than those seen in the wildtype of that strain. One specific example of an *E. coli* phenylalanine over-producer is the *E. coli* strain NST74 (U.S. Pat. No. 4,681,852). Others may include *Corynebacterium glutamicum* [Ikeda, M. and Katsumata, R. Metabolic engineering to produce tyrosine or phenylalanine in a tryptophan-producing *Corynebacterium glutamicum* strain, *Appl. Environ. Microbiol.* (1992), 58 (3), pp. 781-785]. When produced at high levels, phenylalanine is typically excreted into the medium, and thus a phenylalanine over-producing strain is generally also a "phenylalanine excreting strain".

The term "tyrosine over-producing strain" refers to a microbial strain that produces endogenous levels of tyrosine that are significantly higher than those seen in the wildtype of that strain. When produced at high levels, tyrosine is typically excreted into the medium, and thus a tyrosine over-producing strain is generally also a "tyrosine excreting strain".

"Tyrosine" refers to L-tyrosine, "phenylalanine" refers to L-phenylalanine, and "tryptophan" refers to L-tryptophan. These are the L-isomers of the named compounds.

The term "marker" means a gene that confers a phenotypic trait that is easily detectable through screening or selection. A selectable marker is one wherein cells having the marker gene can be distinguished based on growth. For example, an antibiotic resistance marker serves as a useful selectable marker, since it enables detection of cells which are resistant to the antibiotic, when cells are grown on media containing that particular antibiotic. A marker used in screening is, for example, one whose conferred trait can be visualized. Genes involved in carotenoid production or that encode proteins (i.e. beta-galactosidase, beta-glucuronidase) that convert a colorless compound into a colored compound are examples of this type of marker. A screening marker gene may also be referred to as a reporter gene.

The term "making use of the marker" means identifying cells based on the phenotypic trait provided by the marker. The marker may provide a trait for identifying cells by methods including selection and screening.

The term "negative selection marker" means a DNA sequence which confers a property that is detrimental under particular conditions. The property may be detrimental to a plasmid or to a whole cell. For example, expression of a sacB gene in the presence of sucrose is lethal to the expressing cells. Another example is a temperature sensitive origin of replication, which is nonfunctional at nonpermissive temperature such that the plasmid cannot replicate.

Standard recombinant DNA and molecular cloning techniques used here are well known in the art and are described by Sambrook, J., Fritsch, E. F. and Maniatis, T., *Molecular Cloning: A Laboratory Manual*, 2$^{nd}$ ed., Cold Spring Harbor Laboratory: Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

The invention provides a method for making a tyrosine overproducing enteric bacterial strain for use in the production of L-tyrosine by fermentation. The tyrosine over-producer will minimally have the ability to produce chorismate via the aromatic amino acid biosynthetic pathway and will have a disruption in the pheA gene, rendering it non-functional, and will be over-expressing tyrA. In other embodiments the tyrosine overproducing strain will have a variety of other genetic and phenotypic traits, including but not limited to, a gene encoding a DAHP synthase resistant to feedback inhibition by phenylalanine, down regulation of the tyrR gene; resistance to 3-fluorotyrosine; resistance to para-fluorophenylalanine; resistance to β-2-thienylalanine; resistance to tyrosine and resistance to high phenylalanine and high temperature.

The tyrosine overproducing strains of the invention are preferably constructed beginning with a phenylalanine over-producing strain and transforming that strain with a single genetic construct to effect the deletion or disruption of the pheA gene and the over-expression of the tyrA gene. Disruption of the pheA has the effect of blocking carbon to the production of phenylalanine (FIG. 1) and the over-expression of tyrA moves this additional carbon into the part of the pathway dedicated to tyrosine production (FIG. 1). Selection for the additional traits of resistance to various chemicals noted above generally contribute to the robust nature of the strain, further enhancing tyrosine production.

Selection of Host Strain

The invention provides an enteric bacterial strain that overproduces tyrosine and a novel method of the construction of that strain. Essential requirements of the starting strain for construction is that it produces chorismate by the aromatic amino acid pathway (FIG. 1) and comprises a pheA coding region and tyrA coding region in close proximity to each other. Optionally, it will be useful if the selected strain is an over-producer of phenylalanine. Any enteric bacterial strain having the pheA and tyrA coding regions in close proximity to each other are potential hosts for the present one-step process for strain conversion.

Enteric bacteria particularly suitable in the present invention include but are not limited to *Escherichia, Klebsiella, Salmonella, Shigella, Yersinia,* and *Erwinia.* Enteric bacteria are members of the family Enterobacteriaceae and include such members as *Escherichia, Salmonella,* and *Shigella.* They are gram-negative straight rods, 0.3-1.0×1.0-6.0 mm, motile by peritrichous flagella (except for *Tatumella*) or non-motile. They grow in the presence and absence of oxygen and grow well on peptone, meat extract, and (usually) MacConkey's media. Some grow on D-glucose as the sole source of carbon, whereas others require vitamins and/or mineral(s). They are chemoorganotrophic with respiratory and fermentative metabolism but are not halophilic. Acid and often visible gas is produced during fermentation of D-glucose, other carbohydrates, and polyhydroxyl alcohols. They are oxidase negative and, with the exception of *Shigella dysenteriae* 0 group 1 and *Xenorhabdus nematophilus,* catalase positive. Nitrate is reduced to nitrite (except by some strains of *Erwinia* and *Yersina*). The G+C content of DNA is 38-60 mol % ($T_m$, Bd). DNAs from species within most genera are at least 20% related to one another and to *Escherichia coli,* the type species of the family. Notable exceptions are species of *Yersina, Proteus, Providenica, Hafnia* and *Edwardsiella,* whose DNAs are 10-20% related to those of species from other genera. Except for *Erwinia chrysanthemi,* all species tested contain the enterobacterial common antigen (Bergy's Manual of Systematic Bacteriology, D. H. Bergy et al., Baltimore: Williams and Wilkins, 1984).

In enteric bacteria, the pheA and tyrA genes are components of a pheA-tyrA region of the enteric bacterial chromosome and typically are adjacent to each other. The pheA-tyrA region of the *E. coli* chromosome includes the pheA promoter, pheL, which is a 48 bp sequence encoding the leader peptide of chorismate mutase/prephenate dehydratase, the pheA coding region, a rho independent terminator sequence, and in the opposite orientation, the tyrA coding region. The sequence of the pheA-tyrA region from the *E. coli* K12 strain is given as SEQ ID NO:1, which includes the pheA promoter between nucleotides 1 and 80, the pheL coding region between nucleotides 81 and 128, non-coding intergenic sequence between nucleotides 129 and 226, the pheA coding region between nucleotides 227 and 1387, the rho independent terminator between nucleotides 1394 and 1422, and the tyrA coding region between nucleotides 1430 and 2551.

The pheA-tyrA regions of enteric bacteria are highly conserved and methods for the modification of this region will be generally applicable to many members of the class. Within the genus of *Escherichia,* for example, the sequences of the pheA-tyrA regions of *E. coli* strain O157:H7 (SEQ ID NO: 2) and *E. coli* strain CFT073 (SEQ ID NO:3) are each 98% identical to the K12 pheA-tyrA region sequence. Typically the pheA and tyrA coding regions are also individually conserved, demonstrating as close as 97% sequence identity between strains of *E. coli.* These similarities are readily seen in the sequences of the pheA coding regions of K12, O157:H7 and CFT073 strains are given as SEQ ID NOs:4, 5, and 6, respectively and in the sequences of the tyrA coding regions of K12, O157:H7 and CFT073 strains are given as SEQ ID NOs:7, 8, and 9, respectively. The conservation of the pheA and tyrA regions extends to other members of the class of enterics where the proximity of the two coding regions is also a common feature. For example, the corresponding *Yersinia pestis* biovar *Medievalis* str. 91001 protein (SEQ ID NO:10) has 69% identity to the amino acid sequence of the *E. coli* K12 pheA product (SEQ ID NO:11) and the corresponding *Erwinia carotovora* subsp. *atroseptica* SCRI1043 protein (SEQ ID NO:12) has 70% identity to the *E. coli* K12 pheA product.

Any enteric bacterial strain having genes corresponding to pheA and tyrA that are located in close proximity to each other in the chromosome may be a target host for the present method. Particularly suitable are *Escherichia* strains, where the strains designated by the ATCC as #700926, #27325, #31882, #31884, and #13281, are most preferred.

As noted, in one embodiment it will be useful to identify strains that demonstrate robust production of phenylalanine as this suggests a complete and enhanced aromatic amino acid pathway. Specific examples of *E. coli* phenylalanine over-producers are the *E. coli* K12 strains NST37 (ATCC #31882) and NST74 (ATCC #31884), both described in U.S. Pat. No. 4,681,852, incorporated herein by reference. An example of a non-K12 *E. coli* strain with low levels of phenylalanine excretion that may be converted to a tyrosine over-producer using the present method of strain conversion is ATCC#13281 (U.S. Pat. No. 2,973,304), incorporated herein by reference.

Construction of a Tyrosine—Over-Producer: Modification of the Aromatic Amino Acid Biosynthetic Pathway Once a suitable host or strain has been identified, methods for the modification of key elements of the aromatic amino acid pathway may be used to generate a tyrosine over-producing strain.

The relevant elements of the aromatic amino acid pathway are illustrated in FIG. 1. Briefly, the pathway receives carbon ultimately from glucose and synthesis proceeds with the condensation of E4P and PEP to form DAHP, catalyzed by DAHP synthase, which is encoded by the aroFGH set of genes. The pathway proceeds though various intermediates catalyzed by the enzymes encoded to the genes aroB, aroD, aroE, aroL, aroK, aroA and aroC, as shown in FIG. 1, to the point where chorismate is produced. Chorismate is a substrate for both anthranilate synthase (leading to trytophan synthesis) and chroismate mutase leading to the synthesis of first prephenate which itself may be acted on by prephenate dehydratase (encoded by pheA) leading phenylalanine synthesis, or prephenate deydrogenase (encoded by tyrA) leading first to the production of 4-OH-phenylpyruvate and then to tyrosine via catalysis by the tyrB encoded aminotransferase.

Given the elements of the pathway it will be apparent that the challenge in maximizing tyrosine production will be to control the loss of carbon to competing products (phenylalanine, tryptophan) and to optimize carbon flow toward the tyrosine product. Thus, up-regulation of the gene product of tyrA and elimination of gene product of pheA are indicated. Additionally, because wildtype DAHP synthases are known to be inhibited by the end products of the pathway (phenylalanine, tryptophan, tyrosine), and because this is the first enzyme in the pathway controlling carbon flow, it will be useful to obtain strains containing this mutant enzyme to decrease its regulation by end product.

Non-functional pheA-tyrA Over-expression

The proximity of the pheA and tyrA coding regions in the pheA-tyrA region of the chromosome of enteric bacteria makes it possible to alter the expression of both of these coding regions using the present one-step engineering process. The present one-step engineering process includes inactivating the pheA coding region and adding a strong promoter to the tyrA coding region, at the same time. Engineering of pheA and tyrA genes at the same time is accomplished by moving a single engineered chromosomal segment into the chromosome of a host strain to replace the endogenous pheA-tyrA region. This process of altering both genes is accomplished at very high frequency using the single engineered chromosomal segment.

Figure 2:
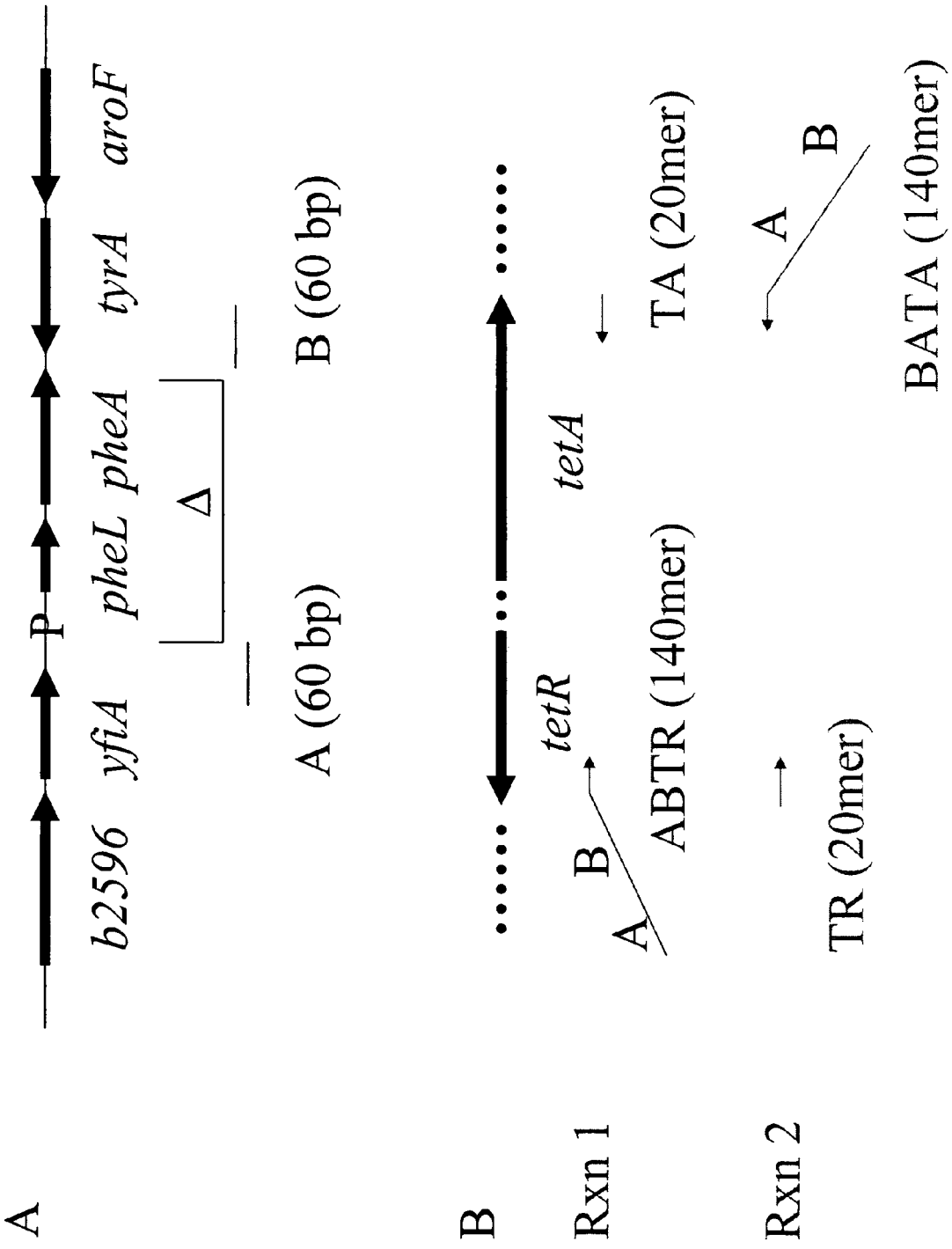
Figure 3:
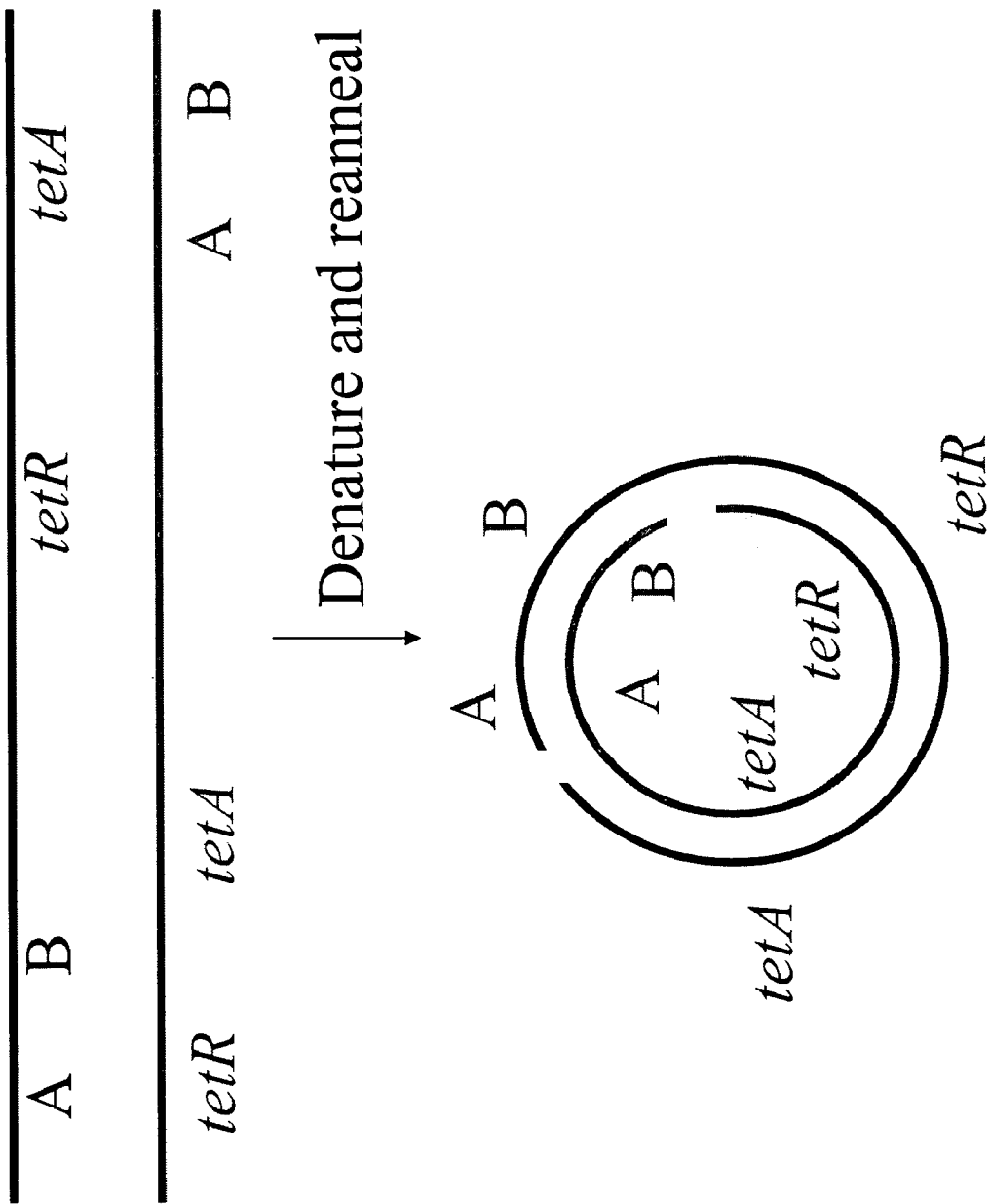
FIG. 3 shows a diagram of the formation of TetRA circles of the PCR products from the primers shown in FIG. 2B.

The engineered chromosomal segment may have any alteration of the pheA sequence which ensures that a functional pheA protein is not produced. Thus the engineered chromosomal segment includes a non-functional pheA construction as a first element. The non-functional pheA construction may have an altered pheA coding region. Altering a coding region to make it non-functional is well known to one skilled in the art. For example, alterations may be mutations, including deletions and insertions. Mutations include a point mutation that introduces a stop codon or changes the reading frame of the protein such that a functional protein is not made. Effective insertions interrupt the reading frame. Deletions include a partial deletion of the region encoding the PheA protein, and a deletion of the full PheA coding region. A deletion may include the pheL coding region as well as the promoter for pheL and pheA expression. A deletion is made by joining the DNA sequences that flank the sequence targeted for deletion, thereby dropping out the flanked sequence. Particularly useful is a deletion which joins the sequence upstream of the pheA promoter to the sequence downstream of the pheA coding region. For example in E. coli, a deletion of the entire pheA gene is made by joining the 3' end of yfiA and intergenic region upstream of the pheA promoter to the intergenic region and 3' end of tyrA downstream of the pheA coding region (see FIG. 2A). This deletion includes the pheL coding region and the promoter driving pheL and pheA expression, along with the entire pheA coding region. The resulting construction may be said to be a non-functional pheA construction, even though no pheA sequence is included.

The chromosomal segment containing the non-functional pheA construction also includes a tyrA coding region expressed from a strong promoter, as a second element. The tyrA coding region may be derived from the target host, or it may be derived from a foreign tyrA gene of a heterologous strain. Any sequence encoding a functional chorismate mutase/prephenate dehydrogenase protein may be used, such as those described in Song, et al. (2005) BMC Biol 3:13). Some examples are the tyrA encoding sequences of E. coli K12 (SEQ ID NO:7), E. coli 0157:H7 (SEQ ID NO:8), E. coli CFT073 (SEQ ID NO:9), Salmonella typhimurium LT2 (SEQ ID NO:13), Photorhabdus luminescens subsp. laumondii TTO1 (SEQ ID NO:14), Shewanella oneidensis MR-1 (SEQ ID NO:15), and Xanthomonas campestris pv. campestris str. ATCC 33913 (SEQ ID NO:16).

In one embodiment it will be useful to use a strong promoter upstream of the tyrA gene to enhance expression. The strong promoter is substituted for the natural tyrA expression promoter, whether from the target host or a heterologous strain, and is operably linked to the tyrA coding region for controlling its expression. Any promoter that gives high levels of expression in the enteric bacteria target host cell may be used, including constitutive and regulated promoters. Such promoters are numerous and familiar to those skilled in the art, and may include for example lac, ara, tet, trp, lambda $P_L$, lambda $P_R$, T7, tac, trc, malE, T3, T4, T5, Streptomyces spp glucose isomerase, Bacillus spp nprM, rrnB, lpp, phoA, proU, cst-1, cadA, nar, cspA, and gyrA. Particularly suitable is the trc promoter.

The trc promoter is an example of a promoter that is that is regulated by the lac repressor. Although these promoters are robust in driving gene expression it may be necessary to inhibit the lac repressor through a gene deletion or targeted mutagenesis. Methods for making a lac deletion are well known in the art and the lac target sequences of many enteric bacteria are commonly available.

The chromosomal segment containing the non-functional pheA construction and the strong promoter expressing tyrA may also include other genetic elements useful to obtain high levels of tyrosine production. These optional elements may include genes for which high expression is desired. For example, aroF, aroG, aroH, aroB, aroD, aroE, aroK aroL, aroA, aroC and/or tyrB genes may be inserted in the chromosomal segment. Strong promoters may be used to express each coding region that is included, or multiple coding regions may form an operon under control of a high expression promoter. Promoters may be used such as those that may be used to express tyrA, described herein above.

In addition, when using an enteric bacterial target host strain that has a pheA-tyrA region including an intervening gene, the chromosomal segment containing the altered pheA and the strong promoter expressing tyrA may also include the intervening gene sequence.

The non-functional pheA construction and the strong promoter expressing tyrA, as well as the optional other elements described above, of the engineered chromosomal segment may be combined in a plasmid or in a bacterial chromosome. PCR and/or cloning methods well known to one skilled in the art may be used to construct the elements individually. Cloning methods may also be used to combine the elements in a plasmid. Alternatively, an element may be introduced into a bacterial chromosome from a plasmid, or an element may be directly constructed in a bacterial chromosome. The elements may then be combined. For example, as described in Example 1, a deletion of the pheA gene may be constructed directly in the bacterial chromosome. In a separate bacterial strain the trc promoter may be directly substituted for the tyrA promoter in a bacterial chromosome. These separately constructed elements in bacterial chromosomes may then be combined using bacteriophage mediate generalized transduction. This process is inefficient and it, as well as combining the elements of the engineered chromosomal segment using any of the known PCR and cloning processes, involves may steps. Once prepared, the engineered chromosomal segment, whether on a plasmid or in a bacterial chromosome, may be inserted into a target host in one step to produce a tyrosine over-producing strain.

The engineered chromosomal segment is inserted in the enteric bacterial target host chromosome at the site of the endogenous pheA-tyrA region, and replaces the endogenous pheA-tyrA region. Insertion of the engineered chromosomal segment may be by any method known to one skilled in the art, such as by phage transduction, conjugation, or plasmid introduction or non-plasmid double or single stranded DNA introduction followed by homologous recombination. In bacteriophage transduction, standard genetic methods for transduction are used which are well known in the art and are described by Miller, J. H., Experiments in Molecular Genetics, Cold Spring Harbor Laboratory Press, Cold Spring Harbor, N.Y. (1972). The engineered chromosomal segment that has been constructed in a bacterial chromosome is packaged in the phage, then introduced to the target host cell through phage infection, followed by homologous recombination to insert the engineered chromosomal segment in the target host cell chromosome.

DNA fragments may be prepared from a bacterial chromosome bearing the engineered chromosomal segment by a method that includes sequences that naturally flank this chromosomal segment in the bacterial chromosome, to provide sequences where homologous recombination will occur. The flanking homologous sequences are sufficient to support homologous recombination, as described in Lloyd, R. G., and K. B. Low (1996; Homologous recombination, p. 2236-2255. In F. C. Neidhardt (ed.), *Escherichia coli* and *Salmonella*: Cellular and Molecular Biology. ASM Press, Washington, D.C.). Typically homologous sequences used for homologous recombination are over 1 kb in length, but may be as short as 50 or 100 bp. DNA fragments containing the engineered chromosomal segment and flanking homologous sequences may be prepared with defined ends, such as by restriction digestion, or using a method that generates random ends such as sonication. In either case, the DNA fragments carrying the engineered chromosomal segment may be introduced into the target host cell by any DNA uptake method, including for example, electroporation, a freeze-thaw method, or using chemically competent cells. The DNA fragment undergoes homologous recombination which results in replacement of the endogenous chromosomal pheA-tyrA region of the target host with the engineered chromosomal segment.

A plasmid may be used to carry the engineered chromosomal segment into the target host cell for insertion. Typically a non-replicating plasmid is used to promote integration. The engineered chromosomal segment is flanked in the plasmid by DNA sequences that naturally flank this chromosomal segment in the bacterial target host genome, to provide sequences where homologous recombination will occur. The flanking homologous sequences are as described above and introduction of plasmid DNA is as described above.

Using any of these methods, homologous recombination may be enhanced by use of bacteriophage homologous recombination systems, such as the bacteriophage lambda Red system [Datsenko and Wanner (2000) Proc. Natl. Acad. Sci. USA 97:6640-6645] and [Ellis et al. (2001) Proc. Natl. Acad. Sci. U.S.A. 98: 6742-6746] or the Rac phage RecE/RecT system [Zhang et al. (2000) Nature Biotechnology 18:1314-1317]. Additionally, methods such as those disclosed in commonly owned U.S. Ser. No. 10/734,936; and U.S. Pat. No. 6,673,567 for gene insertion and mutant selection will be useful in the present application.

In any of the methods, the homologous recombination results in replacement of the endogenous chromosomal pheA-tyrA region of the target host with the engineered chromosomal segment.

Recipient strains with successful insertion of the engineered chromosomal segment may be identified using a marker. Either screening or selection markers may be used, with selection markers being particularly useful. For example, an antibiotic resistance marker may be present in the engineered chromosomal segment, such that when it is transferred to a new host, cells receiving the engineered chromosomal segment can be readily identified by growth on the corresponding antibiotic. Alternatively a screening marker may be used, which is one that confers production of a product that is readily detected. If it is desired that the marker not remain in the recipient strain, it may subsequently be removed such as by using site-specific recombination. In this case site-specific recombination sites are located 5' and 3' to the marker DNA sequence such that expression of the recombinase will cause deletion of the marker.

Regulation of Pathway Elements; DAHP Synthase. tyrR

As noted above, in addition to the elimination of pheA function and the up-regulation of tyrA it may additionally be useful to modulate other elements of the aromatic amino acid pathway to enhance carbon flow to tyrosine. For example, selection for strains that contain DAHP synthase enzymes that are resistant to end product feedback inhibition will be useful. Such strains are known and described in Bongaerts et al. (2001) Metabolic Engineering 3:289-300. For example, *E. coli* has three isozymes of this enzyme encoded by aroG, aroF, and aroH. In wildtype *E. coli*, the aroG-encoded enzyme is inhibited by phenylalanine, the aroF-encoded enzyme is inhibited by tyrosine, and the aroH-encoded enzyme is inhibited by tryptophan. Thus, any of these isozymes may be altered to confer feedback resistance. The aroG397 mutation, disclosed in U.S. Pat. No. 4,681,852, (incorporated herein by reference) is particularly useful in creating a feedback resistant DAHP enzyme. TyrR may also be rendered non-functional, either through mutation in the protein or by blocking expression of the tyrR gene, disclosed in U.S. Pat. No. 4,681,852. TyrR is a regulatory protein that represses the expression of several genes, including aroF, tyrA, aroG, aroL, and tyrB, in the aromatic amino acid biosynthetic pathway [Pittard et al. (2005) Mol. Microbiol. 55:16-26]. The tyrR366 mutation [Camakaris and Pittard (1973) J. Bacteriol. 115: 1135-1144] is particularly useful for inactivating TyrR. The person of skill in the art, knowing the sequence of tyrR in the subject enteric host will readily be able to create disruptive mutants using means well known in the art of gene mutation and disruption (Sambrook supra). The sequence of the tyrR gene for *E. coli* K12 is given herein as SEQ ID NO:31. Additional tyrR sequences are publicly available; see for example

*Escherichia coli* O157:H7 DNA, complete genome:
gi|47118301|dbj|BA000007.2|[47118301]

*Escherichia coli* CFT073, complete genome
gi|26111730|gb|AE014075.1|[26111730]

*Escherichia coli* UTI189, complete genome
gi|191209055|ref|NC_007946.1|[91209055]

*Escherichia coli* W3110 DNA, complete genome
gi|89106884|ref|AC_000091.1|[89106884]

*Salmonella typhimurium* LT2, complete genome
gi|16763390|ref|NC_003197.1|[16763390]

Thus eliminating the repression effect of TyrR, as well as making DAHP synthase feedback resistant, creates more flow of intermediates through the aromatic amino acid biosynthetic pathway to chorismate, which is particularly useful in a host used in the present method for conversion to a tyrosine over-producing strain.

Phenotypic Traits

Increasing the flow of intermediates in the aromatic amino acid biosynthetic pathway may be achieved through selecting resistances in host strains to pathway products and analogs of pathway products. Compounds such as 3-fluorotyrosine, para-fluorophenylalanine, β-2-thienylalanine, tyrosine, and phenylalanine may each be used in screens for resistant cells. As used herein the term "resistance" as applied to the above mentioned compounds is used in a manner consistent with protocols for cell mutagenesis and screening for resistance to these compounds as described in U.S. Pat. No. 4,681,852, incorporated herein by reference. Cells resistant to aromatic amino acid biosynthetic pathway products and analogs of pathway products may have mutations that affect DAHP feedback resistance, TyrR regulation, or other pathway flow controlling factors. The specific mutations that cause the resistance properties need not be completely characterized in order for the cells containing the mutations to be useful as host strains in the present method.

Production of Tyrosine

Enteric bacterial strains that have been converted to tyrosine over-producers by the present method make tyrosine that is excreted into the medium. These strains may be grown in a fermenter where commercial quantities of tyrosine are produced. Strains prepared by the present method produce tyrosine levels that are at least about 26 g/L, where production levels of at least about 50 g/L are expected and levels of at least about 75 g/L are contemplated. Particularly useful are strains prepared by the present method that produce tyrosine levels that are at least about 45 g/L. An *E. coli* strain (DPD4119, see Example 6) producing about 48 g/L of tyrosine in a 10 liter fermentation was made using the present method. In addition to the engineered chromosomal segment ΔpheLA Ptrc-tyrA::Kan$^R$, this strain is resistant to 3-fluorotyrosine, para-fluorophenylalanine, β-2-thienylalanine, tyrosine, high phenylalanine and high temperature. Most preferred are strains prepared by the present method that produce tyrosine levels that are at least about 50 g/L. An *E. coli* strain (DPD4145, Example 8) producing about 54 g/L of tyrosine in a 10 liter fermentation was made using the present method. In addition to the engineered chromosomal segment ΔpheLA Ptrc-tyrA, this strain is resistant to 3-fluorotyrosine, para-fluorophenylalanine, β-2-thienylalanine, tyrosine, high phenylalanine and high temperature, and also has the chromosomal mutation ΔlacIZYA.

Production fermentation or "scale up" fermentation in this disclosure describes greater than 10 L aerobic batch fermentation, and usually 200 L or greater. Where commercial production of tyrosine is desired, a variety of culture methodologies may be applied. For example, large-scale production from a recombinant microbial host may be produced by both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH, dissolved oxygen (DO) and the partial pressure of waste gases such as $CO_2$. Batch and Fed-Batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Fermentation media contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. The carbon substrates may also comprise, for example, alcohols, organic acids, proteins or hydrolyzed proteins, or amino acids. Hence, it is contemplated that the source of carbon utilized in the present fermentation may encompass a wide variety of carbon containing substrates.

Commercial production of tyrosine may also be accomplished with a continuous culture. Continuous cultures are open systems where a defined culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by medium turbidity, is kept constant. Continuous systems strive to maintain steady state growth conditions and thus the cell loss due to medium being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Particularly suitable for tyrosine production is a fermentation regime as follows. The desired strain that is converted to a tyrosine over-producing strain by the present method is grown in shake flasks in semi-complex medium at about 35° C. with shaking at about 300 rpm in orbital shakers and then transferred to a 10 L seed fermentor containing similar medium. The seed culture is grown in the seed fermentor under constant air sparging until $OD_{550}$ is between 10 and 25, when it is transferred to the production fermentor where the fermentation parameters are optimized for tyrosine production. Typical inoculum volumes transferred from the seed tank to the production tank range from 2.0-10% v/v. Typical fermentation medium contains minimal medium components such as potassium phosphate (1.0-3.0 g/l), sodium phosphate (0-2.0 g/l), ammonium sulfate (0-1.0 g/l), magnesium sulfate (0.3-5/0 g/l), a complex nitrogen source such as yeast extract or soy based products (0-10 g/l). Trace amounts of L-phenylalanine and trace elements are also added to the medium at all stages of the seed train for optimal growth of the strain. Carbon sources such as glucose (or sucrose) are continually added to the fermentation vessel on depletion of the initial batched carbon source (10-30 g/l) to maximize tyrosine rate and titer. Carbon source feed rates are adjusted dynamically to ensure that the culture is not accumulating glucose in excess, which could lead to build up of toxic byproducts such as acetic acid. In order to maximize yield of tyrosine produced from substrate utilized such as glucose, biomass growth is restricted by the amount of phosphate that is either batched initially or that is fed during the course of the fermentation. The fermentation is controlled at pH 6.8-7.2 using ammonium hydroxide and either sulfuric or phosphoric acid. The temperature of the fermentor is controlled at 32-35° C. and the DO is maintained around 10-25% air saturation by cascade control using agitation (rpm) and airflow (SLPM) as variables. In order to minimize foaming, antifoam agents (any class—silicone based, organic based etc) are added to the vessel as needed. A particularly suitable antifoam agent used is Biospumex153K. For maximal production of tyrosine, the culture may be induced with small concentrations of isopropyl-β-D-thiogalactopyranoside (IPTG) (0-1.0 mM) at $OD_{550}$ 8-10. An antibiotic, for which there is an antibiotic resistant marker in the strain, such as kanamycin, may be used optionally to minimize contamination.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described, "Maniatis" supra, Enquist supra; and by Ausubel supra.

Standard genetic methods for transduction used in the Examples are well known in the art and are described by Miller, J. H., *Experiments in Molecular Genetics*, Cold Spring Harbor Laboratory Press, Cold Spring Harbor, N.Y. (1972).

The meaning of abbreviations is as follows: "kb" means kilobase(s), "bp" means base pairs, "nt" means nucleotide(s), "hr" means hour(s), "min" means minute(s), "sec" means second(s), "d" means day(s), "L" means liter(s), "ml" means milliliter(s), "μL" means microliter(s), "μg" means microgram(s), "ng" means nanogram(s), "mM" means millimolar, "μM" means micromolar, "nm" means nanometer(s), "μmol" means micromole(s), "pmol" means picomole(s), "ppm" means parts per million, "vvm" means volume air per volume liquid per minute, "CFU" means colony forming unit(s), "NTG" means N-methyl-N'-nitro-N-nitrosoguanidine, "IPTG" means isopropyl β-D-thiogalactopyranoside, "phenylalanine" or "phe" means L-phenylalanine, and "tyrosine" or "tyr" means L-tyrosine. "TFA" is trifluoroacetic acid, "ACN" is acetonitrile, "KanR" is kanamycin resistant, "Phe" is phenylalanine auxotrophic, "Cm" is chloramphenicol, "Kan" is kanamycin, "Tet" is tetracycline, "CIP" is calf intestinal alkaline phosphatase.

Media and Culture Conditions:

Materials and methods suitable for the maintenance and growth of bacterial cultures were found in *Experiments in Molecular Genetics* (Jeffrey H. Miller), Cold Spring Harbor Laboratory Press, Cold Spring Harbor, N.Y. (1972); *Manual of Methods for General Bacteriology* (Phillip Gerhardt, R. G. E. Murray, Ralph N. Costilow, Eugene W. Nester, Willis A. Wood, Noel R. Krieg and G. Briggs Phillips, eds), pp. 210-213, American Society for Microbiology, Washington, D.C. (1981); or Thomas D. Brock in *Biotechnology: A Textbook of Industrial Microbiology*, Second Edition (1989) Sinauer Associates, Inc., Sunderland, Mass. All reagents and materials used for the growth and maintenance of bacterial cells were obtained from Aldrich Chemicals (Milwaukee, Wis.), BD Diagnostic Systems (Sparks, Md.), Invitrogen Corp. (Carlsbad, Calif.), or Sigma Chemical Company (St. Louis, Mo.) unless otherwise specified.

LB medium contains the following in gram per liter of medium: Bacto-tryptone (10), Bacto-yeast extract, (5.0), and NaCl, (10).

Vogel-Bonner medium contains the following in gram per liter: $MgSO_4.7H_2O$, (0.2); citric acid.$1H_2O$, (2.0), $K_2HPO_4$, (10); and $NaNH_4HPO_4.4H_2O$, (3.5).

SOB medium contains the following in gram per liter: Bacto-tryptone, (20), Bacto-yeast extract (5.0), and NaCl (0.5), 250 mM KCl (10 ml), pH adjusted to 7.0 with NaOH.

Above media were either autoclaved or filter-sterilized. Vitamin B1 (thiamin) was added at 0.0001% to Vogel-Bonner medium. $MgCl_2$ was added to SOB medium (5.0 ml of 2M solution per liter). Carbon source and other nutrients and supplements were added as mentioned in the Examples. All additions were pre-sterilized before they were added to the media.

10×MOPS based minimal medium was purchased from Teknova (Half Moon Bay, Calif.). The MOPS minimal medium was made as follows per liter: 10×MOPS (100 ml), 0.132 M $K_2HPO_4$ (10 ml), 20% Glucose (10 ml). Other supplements were added as mentioned in the Examples. All additions were pre-sterilized before they were added to the medium.

SOC medium was obtained from Invitrogen (Carlsbad, Calif.).

Bochner selection plates as modified by Maloy and Nunn (1981, J. Bacteriol. 145:1110-1112) were made as follows:

| | Solution A | |
|---|---|---|
| Bacto tryptone | 5.0 | g |
| Bacto yeast extract | 5.0 | g |
| Chlortetracycline | 50 | mg (4.0 ml of aqueous 12.5 mg/ml, stored dark, 4° C.) |
| Agar | 15 | g |
| $H_2O$ | 500 | ml |
| | Solution B | |
| NaCl | 10 | g |
| $NaH_2PO_4 \cdot H_2O$ | 10 | g |
| $H_2O$ | 500 | ml |

Solutions A and B were autoclaved separately for 20 minutes at 15 psi, then mixed and cooled to pouring temperature. 5.0 ml of 20 mM $ZnCl_2$ and 6.0 ml of 2 mg/ml fusaric acid were added prior to pouring plates.

Molecular Biology Techniques:

Restriction enzyme digestions, ligations, transformations, and methods for agarose gel electrophoresis were performed as described in Maniatis. Polymerase Chain Reactions (PCR) techniques were found in White, B., *PCR Protocols: Current Methods and Applications*, Volume 15 (1993) Humana Press Inc, Totowa, N.J.

HPLC Method

High performance liquid chromatography was performed on an Agilent 1100 (Agilent Technologies, Palo Alto, Calif.). A ZORBAX SB-C18 column (Agilent Technologies) was used. The method used required a column flow rate of 1.00 ml/min, with a stop time of 11 minutes and a post time of 5 minutes. The mobile phase was composed of 95% Solvent A (water+0.1% TFA) and 5% Solvent B (ACN+0.1% TFA). The pump ran within pressure limits defined as a minimum of 20 bar and a maximum of 400 bar. The spectrum was scanned from 100 nm to 380 nm, with signal for tyrosine being recorded at 225 nm and a retention time of 3.598 minutes. Phenylalanine was detected at 215 nm, with a retention time of 4.388 minutes.

Example 1

A Genomic Region in *E. coli* K12 Useful for Construction of Tyrosine Over-Producing Strains This example describes assembly of a region in the *E. coli* K12 chromosome with two features beneficial for tyrosine excretion. The pheA coding region, encoding chorismate mutase/prephenate dehydratase, the pheL coding region, encoding a leader peptide, and the promoter of pheL and pheA were completely deleted. The native promoter of the tyrA gene, encoding chorismate mutase/prephenate dehydrogenase, was replaced with a strong promoter.

The tetRA circle method (depicted in FIGS. 2 to 5) was used to make a complete deletion of pheL, pheA, and the promoter driving their expression. Two 140mer PCR primers were designed having adjacent 60 nucleotide regions of homology for the each of the upstream (3' end of yfiA and intergenic region upstream of the promoter; called A) and downstream (3' end of tyrA and intergenic region; called B) chromosomal regions flanking the desired deletion (see FIG. 2A). One of these 140mer primers (Primer ABTR; SEQ ID NO:17) also had at the 3' end a 20 nucleotide region of homology for the tetR gene encoding the regulatory gene from the transposon Tn10 (see FIG. 2B). The other 140mer primer (Primer BATA; SEQ ID NO:18) also had at the 3' end a 20 nucleotide region of homology for the tetA gene, encoding a tetracycline efflux antiporter that confers tetracycline resistance (see FIG. 2B). In addition, 20mer primers with the same regions of homology to tetR (Primer TR; SEQ ID NO:19) or tetA (Primer TA: SEQ ID NO:20) as at the 3' ends of the ABTR and BATA primers, respectively, were used (see FIG. 2B). These primers were obtained from Sigma Genosys (The Woodlands, Tex.).

The template DNA for PCR reactions using these primers can be obtained from any strain carrying the tetR and tetA genes. It is convenient to use a strain with the transposable element Tn10 located anywhere in the chromosome, such as *E. coli* DPD2112 (zib615::Tn10) or *S. typhimurium* TT2385 (zii614::Tn10). Template DNA, 0.5 µL per PCR reaction, was prepared by resuspending a single colony of DPD4112 or TT2385 in 32.5 µL water and 7.5 µl DMSO and heating at 95° C. for 10 minutes. Two PCR reactions, 50 µL, were performed. For the first PCR reaction, primer TR and BATA were used (3 µL of each primer at 10 pmol/µL) with template DNA from TT2385. For the second PCR reaction, primers TA and ABTR were used (3 µL of each primer at 10 pmol/µL) with template DNA from DPD4112. Water, 18.5 µL and ExTaq Premix (TaKaRa Bio Inc. Otsu, Shiga, Japan), 25 µL, were added. The PCR reaction conditions were 94° C./5 min+35× (94° C./1 min; 60° C./2 min; 72° C./3 min)+72° C./15 min. Products of the expected size, 2151 bp, were generated and purified with Qiaquick PCR purification kit (Qiagen, Valencia, Calif.).

The PCR products were denatured and reannealed to form tetRA circles as follows. Approximately equimolar amounts of each PCR product were combined and NaCl was added to a final concentration of 150 mM. These were heated to 100° C., then cooled slowly over 1 hour to 4° C. in a thermocycler using the following conditions 100° C./5 minutes, 95° C./3 minutes, 18 additional cycles of 3 minutes each with a decrease in temperature of 5° C. each cycle 4° C./hold. The reactions were desalted using a Microcon spin filter with 30,000 MW cutoff (Millipore Corp., Bedford, Mass.). Sterile water was added to 500 µL total volume. The columns were spun at speed 12 in a microfuge for 10 minutes. Water was added, 500 µL, and the columns were spun again. Prior to the final spin, 200 µL water was added. If necessary, 25 µL of water was added to recover the sample. The tetRA circles are open circular molecules carrying the complete tetR and tetA genes and the regions flanking the desired deletion (see FIG. 3).

Figure 4:
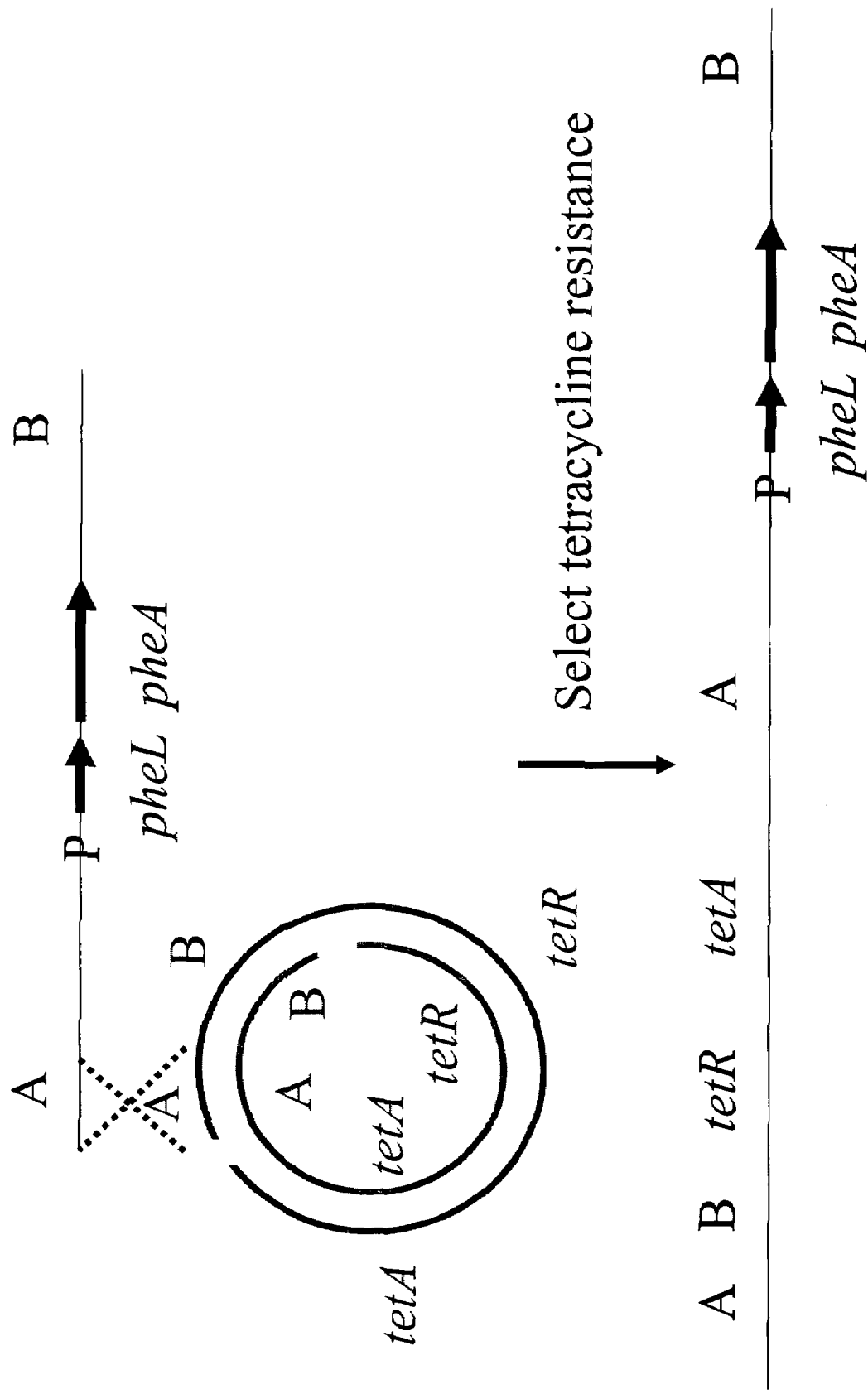
FIG. 4 shows a diagram of a recombination reaction between a TetRA circle and the *E. coli* chromosome, and the resulting chromosomal integration product.

The desalted tetRA circles, 10 µL, were used in electroporation of *E. coli* K12 MG1655 (ATCC#700926). Electroporation competent cells were prepared from a room temperature, stationary overnight 35 mL culture in SOB without magnesium inoculated with a single colony. Cultures were incubated with shaking at 30° C. until the culture reached a reading of 50 on a Klett-Summerson calorimeter with a red filter. The cells were pelleted by centrifugation, 15 minutes, setting 9, 4° C., Sorvall RT6000B, then resuspended with 3.0 ml ice cold water, and transferred to microfuge tubes, which were spun for 30 seconds at 4° C., in a microfuge. Following four more ice cold water washes, the cells were resuspended with 150 µL ice cold water and 50 or 60 µL were used for each electroporation. The electroporation conditions were 0.1 mm cuvette, 25 µF, 1.85 kV, 200 ohms. Then 750 µL SOC was added, the culture transferred to a microfuge tube, and incubated for 4 hours at 30° C. or overnight at 30° C. The electroporated cells were plated on LB plates with 15-20 µg/mL tetracycline and incubated at 37° C. for 1-3 days. In order for colonies to be tetracycline resistant, the tetR and tetA genes must be integrated into the *E. coli* chromosome. This may occur through homologous recombination using the A region homology to the chromosome, as shown in FIG. 4. Likewise, integration is also possible using the B region of homology.

Tetracycline resistant colonies, carrying the integrated tetA and tetR genes (see FIG. 4), were purified on LB plates with 15-20 µg/mL tetracycline. A second, non-selective purification was done by streaking from single colonies selected from the LB plate with tetracycline to LB plates lacking tetracycline. The counter-selection for tetracycline sensitive derivatives, which are resistant to fusaric acid, was done on Bochner selection plates as modified by Maloy and Nunn (1981, J. Bacteriol. 145:1110-1112). Single colonies from the LB plate were streaked to these tetracycline-sensitive selection plates that were incubated at 42° C. for 2 days. Tetracycline sensitive colonies from these plates were purified on LB plates and subsequently tested for growth on minimal plates with or without phenylalanine.

Figure 5:
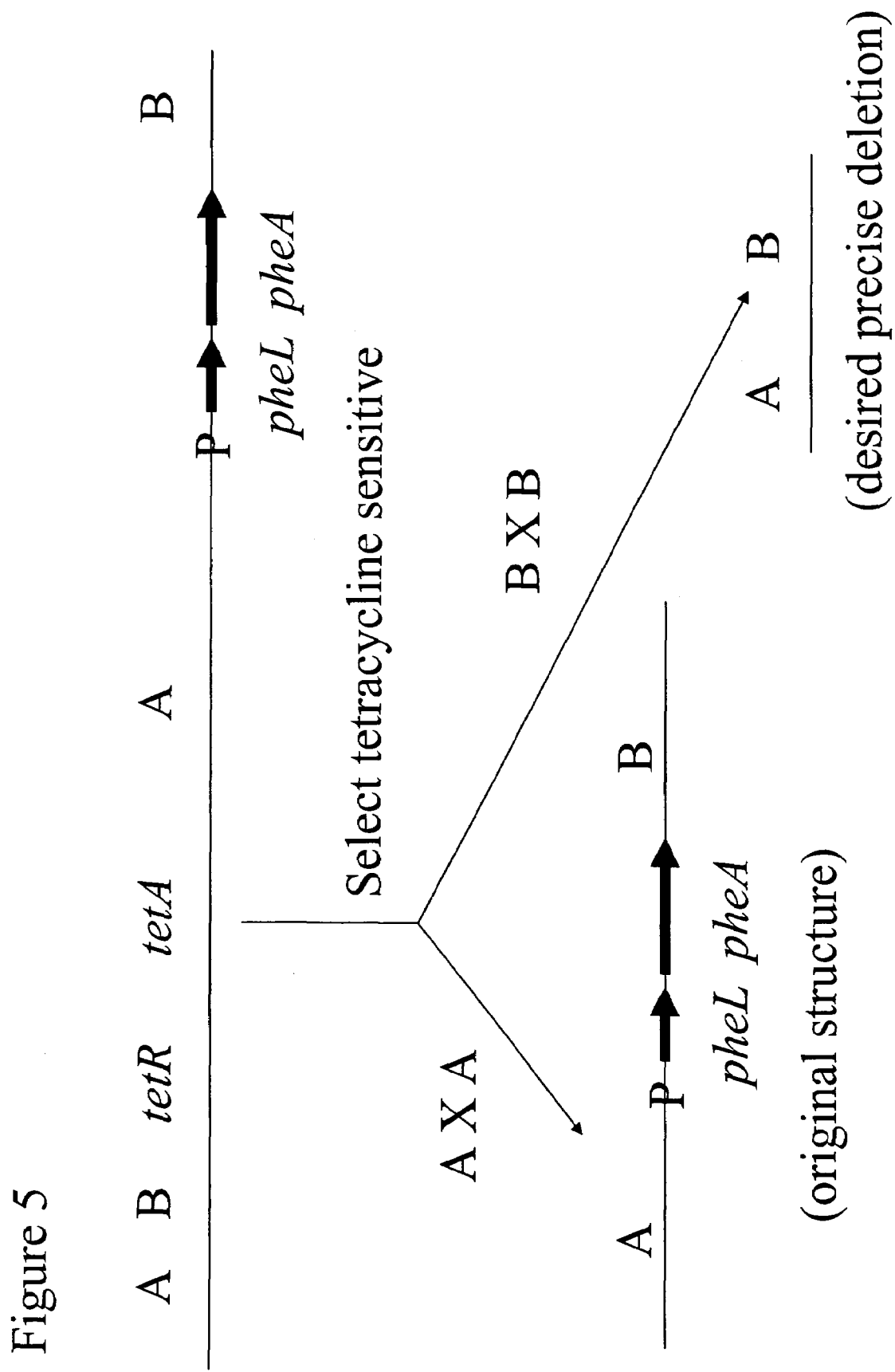
FIG. 5 shows a diagram of two possible outcomes of the tetracycline sensitive counter-selection for a strain carrying the integrated TetRA circle in the pheLA region.

Using this method, 12-18% of the tetracycline-sensitive isolates (from originally tetracycline resistant lines) did not grow on minimal plates without phenylalanine. These phenylalanine auxotrophs were formed by a recombination that removed the tetR and tetA genes and the pheA and pheL coding regions as well as their promoter (B×B recombination as illustrated in FIG. 5). Due to the nature of this method, these phenylalanine auxotrophic strains carried a precise deletion of the pheA and pheL coding regions and their promoter (ΔpheLA). One such phenylalanine auxotrophic strain that was retained was named DPD4072.

The two PCR fragments integration method (PCT Int. Appl WO 2004056973 A2) was used to place the strong trc promoter in the chromosome of *E. coli* K12 such that it would drive expression of the tyrA gene. This method also results in a kanamycin resistance cassette with flanking flp sites located immediately adjacent to the trc promoter (Ptrc).

A first linear DNA fragment (1581 bp) containing a kanamycin selectable marker flanked by site-specific recombinase target sequences (FRT) was synthesized by PCR using the kanamycin resistance gene of plasmid pKD4 (Datsenko and Wanner, PNAS, 97:6640-6645 (2000)) as a template. The primer pairs used were, T-kan(tyrA) (SEQ ID NO:21: 5'-AATTCATCAGGATCTGAACGGGCAGCTGACGGCTC-GCGTGGCTTAACGTCTTGAGCGATTGTGTAG-3') which contains a homology arm (underlined, 46 bp) chosen to match sequences in the upstream region of the aroF stop codon, which is upstream of the tyrA gene in the *E. coli* chromosome, and a priming sequence for the kanamycin resistance gene (20 bp) and B-kan(trc) (SEQ ID NO:22: 5'-AAAACATTATCCAGAACGGGAGTGCGCCTTGAGCG-ACACGAATATGA ATATCCTCCTTAGTTCC-3') that contains a homology arm (underlined, 42 bp) chosen to match sequences in the 5'-end region of the trc promoter DNA fragment and a priming sequence for the kanamycin resistance gene (22 bp). A second linear DNA fragment (163 bp) containing a trc promoter comprised of the −10 and −35 consensus sequences, lac operator (lacO), and ribosomal binding site (rbs) was synthesized by PCR from plasmid pTrc99A (Invitrogen, Carlsbad, Calif.) with primer pairs, T-trc(kan) (SEQ ID NO:23: 5'-CTAAGGAGGATATTC-ATATTCGTGTCGCTCAAGGCGCACT-3') that contains a homology arm (underlined, 18 bp) chosen to match sequences in the downstream region of the kan open reading frame and a priming sequence for the trc promoter (22 bp) and B-trc(tyrA) (SEQ ID NO:24: 5'-CGACTTCATCAATTT-GATCGCGTAATGCGGTCAATTCAGCAACCATGGTCT-GTTTCCTGTGTGAAA-3') that contains a homology arm (underlined, 46 bp) chosen to match sequences in the downstream region of the tyrA start codon and a priming sequence for the trc promoter (20 bp). The underlined sequences illustrate each respective homology arm, while the remainder are the priming sequences for hybridization to complementary nucleotide sequences on the template DNA for the PCR reaction. Standard PCR conditions were used to amplify the linear DNA fragments with MasterAmp™ Extra-Long DNA polymerase (Epicentre, Madison, Wis.) as follows;

| PCR reaction: | PCR reaction mixture: |
| --- | --- |
| Step1 94° C. 3 min | 1 µL plasmid DNA |
| Step2 93° C. 30 sec | 25 µL 2X PCR buffer #1 |
| Step3 55° C. 1 min | 1 µL 5'-primer (20 µM) |
| Step4 72° C. 3 min | 1 µL 3'-primer (20 µM) |
| Step5 Go To Step2, 25 cycles | 0.5 µL MasterAmp ™ DNA polymerase |
| Step6 72° C. 5 min | 21.5 µL sterilized dH$_2$O |

After completing the PCR reactions, PCR products were purified using Mini-elute QIAquick Gel Extraction Kit™ (QIAGEN Inc. Valencia, Calif.). The DNA was eluted with 10 µL of distilled water by spinning at top speed two times. The concentration of PCR DNA sample was about 0.5-1.0 µg/µL.

*E. coli* MC1061 strain carrying a λ-Red recombinase expression plasmid was used as a host strain for the recombination of PCR fragments. The strain was constructed by transformation with a λ-Red recombinase expression plasmid, pKD46 (amp$^R$) (Datsenko and Wanner, supra) into the *E. coli* strain MC1061. The λ-Red recombinase in pKD46 is comprised of three genes: exo, bet, and gam, expressed under the control of an arabinose-inducible promoter. Transformants were selected on 100 µg/mL ampicillin LB plates at 30° C. The electro-competent cells of *E. coli* MC1061 strain carrying pKD46 were prepared as follows. *E. coli* MC1061 cells carrying pKD46 were grown in SOB medium with 100 µg/mL ampicillin and 1 mM L-arabinose at 30° C. to an OD$_{600}$ of 0.5, followed by chilling on ice for 20 min. Bacterial cells were centrifuged at 4,500 rpm using a Sorvall® RT7 PLUS (Kendro Laboratory Products, Newton, Conn.) for 10 min at 4° C. After decanting the supernatant, the pellet was resuspended in ice-cold water and centrifuged again. This was repeated twice and the cell pellet was resuspended in 1/100 volume of ice-cold 10% glycerol.

Both the kanamycin marker PCR products (~1.0 µg) and trc promoter PCR products (~1.0 µg) were mixed with 50 µL of the competent cells and pipetted into a pre-cooled electroporation cuvette (0.1 cm) on ice. Electroporation was performed by using a Bio-Rad Gene Pulser set at 1.8 kV, 25 µF with the pulse controller set at 200 ohms. SOC medium (1.0 mL) was added after electroporation. The cells were incubated at 37° C. for 1.0 hour. Approximately one-half of the cells were spread on LB plates containing 25 µg/mL kanamycin. After incubating the plate at 37° C. overnight, six kanamycin resistant transformants were selected. The chromosomal integration of both the kanamycin selectable marker and the trc promoter in the front of the tyrA gene was confirmed by PCR analysis. A colony of transformants was resuspended in 25 µL of PCR reaction mixture containing 23 µL SuperMix (Invitrogen), 1.0 µL of 5'-primer T-ty(test) (SEQ ID NO:25: 5'-CAACCGCGCAGTGAAATGAAATACGG-3') and 1.0 µL of 3'-primer B-ty(test) (SEQ ID NO:26: 5'-GCGCTCCGGAACATAAATAGGCAGTC-3'). Test primers were chosen to amplify regions located in the vicinity of the integration region. The PCR analysis with T-ty(test) and B-ty(test) primer pair revealed the expected size product of 1,928 bp on a 1.0% agarose gel. The resultant recombinant with Ptrc-tyrA::Kan$^R$ was called *E. coli* WS158.

Generalized transduction using P1clr100Cm phage (J. Miller. Experiments in Molecular Genetics. 1972. Cold Spring Harbor Press) was used to combine the Ptrc-tyrA::Kan$^R$ with ΔpheLA. Phage grown on *E. coli* strain WS158 carrying Ptrc-tyrA::Kan$^R$ was used as the donor, *E. coli* strain DPD4072 with ΔpheLA was the recipient, and selection was for Kanamycin resistance on LB plates with 12.5 µg/mL kanamycin. The transductants selected on 12.5 µg/mL were subsequently able to grow on plates containing 25 µg/mL kanamycin. The Kan$^R$ transductant colonies were screened for phenylalanine auxotrophy by testing for growth on minimal medium with and without phenylalanine. Of 313 Kan$^R$ colonies obtained, 4 required phenylalanine for growth. The presence of the Ptrc-tyrA::Kan$^R$ in these 4 strains was confirmed by PCR amplifications. Thus, the observed cotransduction frequency of pheA and tyrA was >98%, as expected for adjacent genes. The Kan$^R$, Phe$^-$ strains, each of which was a P1clr100Cm lysogen, were retained and named DPD4081, DPD4082, DPD4083, and DPD4084. Subsequent P1-mediated generalized transductions using these newly constructed ΔpheLA Ptrc-tyrA::Kan$^R$ double mutant strains as a donors will be expected to have >98% frequency of delivering both ΔpheLA and Ptrc-tyrA::Kan$^R$. Thus, for most Kan$^R$ transductants, pheA will be converted to ΔpheA and tyrA to Ptrc-tyrA::Kan$^R$.

*E. coli* K12 strains, DPD4081 and DPD4082, described above, were originally derived from MG1655, a tyrosine non-excreting strain, and carry ΔpheLA and Ptrc-tyrA::Kan$^R$. These strains were tested for tyrosine excretion under conditions of limiting phenylalanine by conducting a cross feeding test using a tyrosine auxotrophic strain, AT2471 (CGSC

4510). Accordingly, DPD4081 or DPD4082 were streaked on a Vogel-Bonner minimal medium plate with glucose as a carbon source and vitamin B1 supplemented. Very near, but not touching, AT2471 was streaked. Following incubation for one day at 30° C. plus two days at room temperature, there was good growth of AT2471 only on the part of the streak nearest DPD4081 or DPD4082. Strain AT2471 streaked alone on these plates did not grow. Thus, tyrosine produced by DPD4081 or DPD4082 allowed growth of AT2471 and hence these results indicated that tyrosine was excreted by DPD4081 and DPD4082.

Example 2

One-Step Conversion of Tyrosine Non-Excreting *E. coli* K12 Strain to Tyrosine Excreting Strain This example describes the conversion of a tyrosine non-excreting *E. coli* strain to a tyrosine excreting strain using a one-step process that introduces the ΔpheLA and Ptrc-tyrA::$Kan^R$ chromosomal region.

The tyrosine non-excreting *E. coli* K12 strain, W3110 (ATCC#27325), was used as a recipient in a generalized transduction using a P1clr100Cm lysate of *E. coli* DPD4081, which is an *E. coli* K12 strain that carries the ΔpheLA Ptrc-tyrA::$Kan^R$ chromosomal region described in Example 1. Selection was made for Kanamycin resistance on LB plates containing 12 or 25 μg/ml kanamycin. A $Kan^R$, phenylalanine auxotrophic transductant was retained and named DPD4198. This strain was tested for tyrosine production by growing cultures in duplicate shake flasks at 37° C., 300 rpm using MOPS buffered minimal medium with 2 g/L glucose and 10 μg/ml phenylalanine. Tyrosine and phenylalanine in the culture supernatants were measured by HPLC at 22 hours, when glucose was depleted. Each of the duplicate culture supernatants had 78 ppm of tyrosine and 7 ppm of phenylalanine. Thus a significant amount of tyrosine was produced and excreted into the culture medium by *E. coli* strain DPD4198, which was derived in one transduction step from W3110.

Example 3

One-Step Conversion of *E. coli* K12 Phenylalanine Excreting Strains to Tyrosine Excreting Strains This example describes use of the ΔpheLA and Ptrc-tyrA::$Kan^R$ chromosomal region of Example 1 to convert phenylalanine excreting strains derived from *E. coli* K12 to tyrosine excreting strains in one step.

Two previously described (U.S. Pat. No. 4,681,852) phenylalanine excreting *E. coli* K12 strains, NST37 (ATCC #31882) and NST74 (ATCC #31884) were obtained from the ATCC. These strains were converted in one step to tyrosine excreting strains. Strains NST37 and NST74 were used as recipients in a generalized transduction using a P1clr100Cm lysate of *E. coli* DPD4081 or DPD4083, which are *E. coli* K12 strains that carry the ΔpheLA Ptrc-tyrA::$Kan^R$ chromosomal region described in Example 1. Selection was made for Kanamycin resistance on LB plates containing 12 or 25 μg/ml kanamycin. The transductants were screened for phenylalanine auxotrophy. Eight of eight $Kan^R$ transductants were also Phe A $Kan^R$, Phe transductant of NST37 was retained and named DPD4193. Likewise, a $Kan^R$, Phe⁻ transductant of NST74 was retained and named DPD4195. Several shake flask studies at 37° C. or 32° C., 300 rpm, in MOPS buffered medium with 2 g/L glucose and other medium amendments as noted in Tables 1 and 2 were conducted on the parental strains as well as the converted strains. Supplements to the media were as required for growth according to the genotype of the strain, with the exception of vitamin B1, which was added in one experiment to test for growth improvement. Tyrosine and phenylalanine in the culture supernatants were measured by HPLC at the times noted in the tables and the concentrations detected are given in Tables 1 and 2 ([Phe] ppm and [Tyr] ppm). No tyrosine was detected in the supernatants of the cultures in Table 1 and low levels of phenylalanine were detected in the supernatants of the cultures in Table 2.

TABLE 1

Phenylalanine excretion in parental strains.
*E. coli* K12 Phenylalanine excreting strains

| Strain | Genotype | MOPS glucose 2 g/L medium with: | Expt. 1 37° C., 24 hr [Phe] ppm, | Expt. 2, 37° C. [Phe] ppm |
|---|---|---|---|---|
| NST37 | aroH367 tyrR366 tna-2 lacY5 aroF394(fbr) malT384 pheA101(fbr) pheO352 aroG397(fbr) tyrA4 trpE382 | trp 10 μg/mL tyr 10 μg/mL | 118 +/− 14 | 140 (42 hr) |
| NST74 | aroH367 tyrR366 tna-2 lacY5 aroF394(fbr) malT384 pheA101(fbr) pheO352 aroG397(fbr) | no addition | 7 +/− 1 | 44 (42 hr) |
| NST74 | aroH367 tyrR366 tna-2 lacY5 aroF394(fbr) malT384 pheA101(fbr) pheO352 aroG397(fbr) | no addition | 24 +/− 1 | 49 (22 hr) |

TABLE 2

Tyrosine excretion in converted strains.
Experiment 2 in Table 2 was done simultaneously to experiment 2 in Table 1.
E. coli NST-derived Tyrosine excreting strains

| Strain | Genotype | MOPS glucose 2 g/L medium with: | Expt 2 37° C. [Tyr] ppm | Expt. 3 32° C. Biological Replicates* [Tyr] ppm | Expt. 4 37° C. Biological Replicates*, B1 added, [Tyr], ppm |
|---|---|---|---|---|---|
| DPD 4193 (from NST37) | E. coli K12 aroH367 tyrR366 tna-2 lacY5 malT384 aroG397(fbr) trpE382 Delta(pheA) Ptrc-tyrA::Kan$^R$ | trp 10 μg/mL phe 10 μg/mL | 180 (42 hr) | 111 (55 hr) 40 (46 hr) | 56 (24 hr) |
| DPD 4195 (from NST74) | E. coli K12 aroH367 tyrR366 tna-2 lacY5 malT384 aroG397(fbr) Delta(pheA) Ptrc-tyrA::Kan$^R$ | phe 10 μg/mL | 147 (42 hr) | 44 (55 hr) 67 (55 hr) | 62 (24 hr) 62 (24 hr) |

*Biological Replicates indicates independent shake flasks.

Thus, tyrosine was clearly excreted by the strains carrying the ΔpheLA Ptrc-tyrA::Kan$^R$ chromosomal region, which was acquired in one transduction step.

Example 4

Conversion of a Non-K12 Low Level Phenylalanine Excreting E. coli Strain to a Tyrosine Excreting Strain This example describes use of the ΔpheLA and Ptrc-tyrA::Kan$^R$ chromosomal region of Example 1 to convert a low level phenylalanine excreting E. coli strain, which is not derived from E. coli K12, to a tyrosine excreting strain in one step.

A non-K12 E. coli strain was that excretes a low level of phenylalanine (U.S. Pat. No. 2,973,304) was obtained from the ATCC (ATCC#13281) and renamed DPD4130. Strain DPD4130, which requires tyrosine for growth, was used as a recipient in a generalized transduction using a P1clr100Cm lysate of E. coli DPD4083, an E. coli K12 strain that carries the ΔpheLA Ptrc-tyrA::Kan$^R$ chromosomal region described in Example 1. Selection was on LB plates with 25 μg/ml kanamycin. Large and very small colonies were observed. Two of the large colonies were purified and shown to be phenylalanine auxotrophs that did not require tyrosine for growth. When streaked on plates without phenylalanine these strains did not grow, while when streaked on plates without tyrosine, they did grow, unlike the parental strain. These two transductants, named DPD4114 and DPD4115, were also shown to ferment sucrose using MacConkey agar indicator plates, which is a characteristic of the initial strain, DPD4130, but not of E. coli K12 strains.

Strains DPD4114 and DPD4115 were tested for tyrosine excretion under conditions of limiting phenylalanine by conducting a cross feeding test using a tyrosine auxotrophic strain, AT2471 (CGSC #4510). Accordingly, DPD4114 and DPD4115 were each streaked on a Vogel-Bonner minimal medium plate with glucose as a carbon source and vitamin B1 supplemented. Very near, but not touching, AT2471 was streaked. Following incubation for one day at 32° C., there was good growth of AT2471 only on the part of the streak nearest DPD4114 or DPD4115. A tyrosine non-excreting E. coli K12 strain, MG1655, did not allow any growth of AT2471 under the same conditions. Hence these results indicated that tyrosine was excreted by DPD4114 and DPD4115. Thus, in this example, a phenylalanine excreting and tyrosine requiring strain was converted to a phenylalanine requiring and tyrosine excreting strain in one step.

Example 5

Conversion of a High Level Phenylalanine Excreting E. coli Strain to a Tyrosine Excreting Strain This example describes use of the ΔpheLA and Ptrc-tyrA::Kan$^R$ chromosomal region of Example 1 to convert a high level phenylalanine excreting E. coli strain to a tyrosine excreting strain in one transduction step.

A high-level phenylalanine excreting strain was obtained in several steps. E. coli strain DPD4130 was subjected to mutagenesis using NTG followed by selection for analogue resistance using 3-fluorotyrosine. The resultant 3-fluorotyrosine resistant strain was mutagenized with NTG and selected for resistance to the analogue para-fluorophenylalanine. The resultant 3-fluorotyrosine and para-fluorophenylalanine resistant strain was mutagenized with NTG and selected for resistance to the analogue β-2-thienylalanine. The resultant 3-fluorotyrosine, para-fluorophenylalanine and β-2-thienylalanine resistant strain was mutagenized with NTG and a tyrosine auxotroph (Tyr$^-$) was isolated. A tyrosine resistant mutant of the 3-fluorotyrosine, para-fluorophenylalanine, β-2-thienylalanine resistant and Tyr$^-$ strain was selected. The resultant tyrosine, 3-fluorotyrosine, para-fluorophenylalanine, β-2-thienylalanine resistant and Tyr$^-$ strain was selected for resistance to phage P1, Type I phage, and Type II phage and then a xylose negative mutant was isolated. The resultant strain was transformed with the plasmid pJN307, encoding a feedback resistant pheA gene with a deleted attenuator (described in Nelms et al. Appl Environ Microbiol. 1992 58(8):2592-8 and in U.S. Pat. No. 5,120, 837). Finally a Tyr$^+$ prototroph was isolated and then a strain resistant to high phenylalanine and high temperature was obtained and named DPD4003. E. coli strain DPD4003 produces >40 g/l phenylalanine from glucose in fermentation.

The phenylalanine excreting strain DPD4003 was resistant to phage P1. Thus, a phage P1-sensitive revertant was isolated so that P1 mediated generalized transduction could be used to introduce new genetic material. E. coli DPD4003 was infected with P1clr100Cm and the rare $Cm^R$ colonies were isolated. These spontaneous, putative P1-resistant revertants were then selected for growth at 42° C. to cure the temperature-sensitive lysogenic phage. One of these temperature-resistant and Cm-sensitive isolates, designated DPD4110, was confirmed to be sensitive to P1. This confirmation was done by testing the frequency of $Cm^R$ colonies after infection by P1clr100Cm. A similar number of $Cm^R$ colonies were obtained for infection of DPD4110 as were obtained for infection of DPD4130, which is the original parental strain of DPD4003.

E. coli strain DPD4110 contains plasmid pJN307, which carries a kanamycin resistance gene. Thus, a derivative of DPD4110 lacking this small plasmid was isolated. This was accomplished by treating DPD4110 with sub-lethal concentrations (50 or 75 µg/ml) of novobiocin for 22 hours in LB medium at 37° C. Single colonies from these cultures were tested for kanamycin-sensitivity and two such derivatives were retained. The loss of plasmid DNA in the $Kan^S$ strains, DPD4112 and DPD4113, was confirmed by agarose gel electrophoresis of total DNA.

Strain DPD4112 was used as a recipient in a generalized transduction using a P1clr100Cm lysate of E. coli DPD4083, an E. coli K12 strain that carries the ΔpheLA Ptrc-tyrA::$Kan^R$ chromosomal region described in Example 1. A high concentration of donor P1 phage, 100 µl of the phage lysate, and very low concentration of kanamycin, 3.0 µg/ml, were used. Spontaneous low-level kanamycin-resistant colonies, which were unable to grow in the presence of 25 µg/ml, kanamycin, occurred in this procedure. One colony that subsequently grew on high level, 25 µg/ml, kanamycin was obtained. This transductant was shown to be a phenylalanine auxotroph and to ferment sucrose, as expected for a strain resulting from transduction of the ΔpheLA Ptrc-tyrA::$Kan^R$ chromosomal region into the recipient DPD4112. This new strain, DPD4118, was also a P1clr100 lysogen, as indicated by its resistance to chloramphenicol and its temperature sensitivity. Thus, selection for growth at 42° C. was done. Two resultant strains, DPD4119 and DPD4120, were each shown to be chloramphenicol sensitive and to excrete tyrosine in a plate assay for cross feeding of the tyrosine auxotrophic E. coli strain, AT2471.

E. coli strains DPD4119 and DPD4120 were tested for tyrosine production in shake flasks. These experiments were done using a MOPS buffered media with 2.0 g/L glucose and 10 µg/ml phenylalanine at 32° C. and 300 rpm. After 24 hours, the glucose was depleted and tyrosine and phenylalanine in the medium were measured by HPLC. Table 3 summaries the results.

TABLE 3

Tyrosine and phenylalanine excretion in converted high phenylalanine excreting strain.

| E. coli strain | Tyrosine (ppm) | Phenylalanine (ppm) |
| --- | --- | --- |
| DPD4119 (ΔpheLA Ptrc-tyrA::$Kan^R$ of DPD4112) | 297 | 230 |
| DPD4120 (ΔpheLA Ptrc-tyrA::$Kan^R$ of DPD4112) | 279 | 217 |

Thus, E. coli DPD4119 and DPD4120 excreted substantial amounts of tyrosine. That phenylalanine was also excreted despite the complete deletion of pheA is not surprising because it is well-known that accumulated prephenate can be non-enzymatically converted to phenylpyruvate, which is then transaminated to phenylalanine [Young, I. G., F. Gibson, and C. G. MacDonald (1969) Biochim Biophys Acta 192:62-72] and [Zamir, L. O., R. Tiberio, and R. A. Jensen (1983) Tetrahedron Lett 28:2815-2818].

Example 6

Fermentation of Strain DPD4119 for Production of Tyrosine

This example describes high-level tyrosine production by E. coli strain DPD4119 in fermentation. Strain DPD4119 was grown in 500 ml of medium in a 2.0 L shake flask at 35° C., 300 rpm for approximately 8.0 h, before it was transferred to a 10 L seed fermentor (Biostat C) for further cultivation. Shake-flask medium contained (in gram per liter): $KH_2PO_4$, (1.0); $Na_2HPO_4$, (3.0); $(NH_4)_2SO_4$, (3.0); $MgSO_4.7H_2O$, (0.3); Yeast Extract, (2.0); MOPS (15.7); L-Phe, (0.1); glucose, (15) and kanamycin. (50 mg/l). The batched seed fermentor medium contained (in gram per liter): $KH_2PO_4$. (2.1); $Na_2HPO_4$, (0.9); $(NH_4)_2SO_4$, (0.5); Thiamine, (1.0 mg/l); L-Phe, (0.2), and antifoam agent (Biospumex153K) 1.0 ml/l. Following sterilization, glucose was added to a final concentration of 20 g/l, yeast extract at 1.0 g/l, kanamycin at 50 mg/l, 16 ml of trace elements, and $MgSO_4.7H_2O$ at 2 mM. Temperature and pH was maintained at 35° C. and 6.8, respectively, during the entire duration of the fermentation. When the cell density reached $OD_{550}$ 23, an aliquot (0.5 l) of the culture from the seed fermentor was transferred to another 10 L production fermentor (Biostat C) which contained similar medium composition as the seed fermentor. Fermentation parameters for the production fermentor were as follows: Dissolved Oxygen at 10%, airflow between 0.5-1 vvm, temperature 35° C., and pH 6.8. Glucose (60%) was fed during the fed-batch stage such that residual glucose level in the fermentor was maintained below 0.5 g/l. Antifoam agent Biospumex153K was added on a need basis. To maximize production of tyrosine, the culture was induced with 1.0 mM IPTG at $OD_{550}$ 9.0, and 16 ml of 1.0 M $MgSO_4.7H_2O$ was spiked into the vessel at this time. Samples were drawn from the fermentor periodically and analyzed for tyrosine, L-phenylalanine and biomass. Results are shown in Table 4.

TABLE 4

Fermentation products of Strain DPD4119)

| Elapsed Fermentation Time (h) | L-Tyrosine (g/l) | L-Phenylalanine (g/l) | Biomass OD550 |
| --- | --- | --- | --- |
| 44 | 41.18 | 2.63 | 63.30 |
| 48 | 45.42 | 3.24 | 60.90 |
| 52 | 47.93 | 3.45 | 55.50 |
| 56 | 48.96 | 3.53 | 53.00 |

The above documented fermentation protocol for production of tyrosine is given as an example. Anyone trained in the field could easily generate modifications of this protocol based on prior art to further optimize tyrosine rate and titers. One such modification as an example could include changes to the medium components and compositions or changes to the glucose feeding profile and/or strategy during the fed-batch mode of operation.

Thus, E. coli strain DPD4119, which was derived from a high-level phenylalanine producing strain and carries the ΔpheLA Ptrc-tyrA::Kan$^R$ chromosomal region described in Example 1, produced greater than 45 g/l tyrosine in fermentation.

Example 7

Deletion of LacI, Encoding the Lac Repressor, to Obviate the IPTG Requirement This example describes an improved tyrosine excreting strain that in addition to the ΔpheLA Ptrc-tyrA chromosomal region also carries a deletion of lac, encoding the Lac Repressor, such that expression of tyrA from the trc promoter is not repressed in the absence of IPTG.

*E. coli* strain DPD4119 is not optimal for further genetic manipulations because it has an active DNA restriction system that differs from the *E. coli* K12 restriction system. Accordingly, strain DPD4112, a predecessor strain of DPD4119 (Example 5) was subjected to selection for decreased DNA restriction activity using λKAN2, which is a λ insertion vector λ NM459 with cI857 that encodes a temperature sensitive repressor and a Kan$^R$ gene cloned in the Eco RI site. A number of kan$^R$ and temperature sensitive mutants of DPD4112 were obtained following lysogenization and selection with λKAN2. Confirmation of reduced restriction was done by cross streaking against λ507, a clear, cI test phage with a different immunity (imm21). Restriction deficient isolates were those that allowed phage growth and subsequently cell lysis and reduced bacterial growth in the area of the cross streak. After removal of the prophage by growth at 42° C., two Kan$^S$ strains were retained and archived as DPD6006 and DPD6007. In comparative titrations of these strains with a λ507 test phage, strain DPD6007 had the greatest reduction in restriction activity, as seen in the Table 5 below.

TABLE 5

Test of restriction activity by phage growth.

| Strain | λTiter per ml |
| --- | --- |
| DPD6006 | $1.5 \times 10^8$ |
| DPD6007 | $8.0 \times 10^8$ |

*E. coli* strain DPD6007, a restriction deficient strain derived from a predecessor of DPD4119, was used to construct a strain that is equivalent to DPD4119 except for the restriction deficiency. Thus, DPD6007 was the recipient strain in a P1 transduction using a P1clr100Cm lysate of *E. coli* DPD4083, a K12 strain that carries the ΔpheLA Ptrc-tyrA::Kan$^R$ chromosomal region. Selection was made for kanamycin resistance using various concentrations of kanamycin in the selection plates and various concentrations of phage. A total of >15 transductants able to grow on 25 ug/ml kanamycin were obtained after 2 days incubation at 30° C. Fifteen of these were tested to see if a lysogen of P1clr100Cm had been concomitantly formed. Seven Kan$^R$ strains were temperature resistant and sensitive to chloramphenicol, indicating that they were not carrying P1clr100Cm. All seven of the non-lysogenic strains were phenylalanine auxotrophs indicating co-transduction of the pheLA deletion with kanamycin-resistance. Three of these strains, DPD4127, DPD4128, and DPD4129 were saved and tested in shake flasks for tyrosine production. For this shake flask comparison, the strains were grown in MOPS medium using 2 g/L glucose as the carbon source and supplemented with an initial concentration of 15 μg/ml phenylalanine. The concentration of tyrosine and phenylalanine was measured by HPLC after 24 hours incubation at 32° C., at which time the glucose was depleted. Very similar tyrosine production was observed for all strains tested (see Table 6 below), indicating that the restriction deficiency did not interfere with the tyrosine production pathway, as expected.

TABLE 6

Tyrosine excretion in restriction deficient strains.

| *E. coli* strain | Tyrosine (ppm) | Phenylalanine (ppm) |
| --- | --- | --- |
| DPD4119 | 180 | 90 |
| DPD4127 | 176 | 93 |
| DPD4128 | 173 | 87 |
| DPD4129 | 174 | 87 |

The kanamycin resistance cassette in the above strains is flanked by frt sites and thus can be removed using Flp recombinase (Datsenko, supra). This procedure, which leaves an FRT scar in the chromosome, was done using plasmid pCP20 (Datsenko, supra) in strain DPD4128 to generate strain DPD7001. No detrimental effect on tyrosine production is expected by this change. This was tested in shake flasks using MOPS medium with 2 g/L glucose and 10 μg/ml phenylalanine with incubation at 32° C. Biological duplicates of DPD4119 and DPD7001 were tested and technical replicates of 22 hour samples were taken, thus resulting in four measurements for each strain. The means and standard deviation of these measurements are given in Table 7 below.

TABLE 7

Tyr and phe excretion in FRT scar strains.

| | Tyrosine | | Phenylalanine | |
| --- | --- | --- | --- | --- |
| | Mean | St Dev | Mean | St Dev |
| DPD4119 | 290 | 13 | 87 | 2 |
| DPD7001 | 271 | 5 | 83 | 1 |

As expected, strains DPD4119 and DPD7001 have very similar tyrosine production.

Expression of tyrA, which encodes chorismate mutase and prephenate dehydrogenase activities, in the tyrosine producing strains DPD4119 and DPD7001, is driven from a chromosomal trc promoter. Thus, the LacI repressor may reduce tyrA expression and consequently limit tyrosine production and accordingly IPTG was routinely added to fermentations with DPD4119. It was expected that inducible expression of tyrA was not necessary in these strains. In fact, continuous high tyrA expression may be beneficial, so that intermediates do not accumulate behind the bottleneck that occurs when tyrA levels are limiting. Thus, to eliminate the need for IPTG and to give higher level of tyrA expression, the chromosomal lacI gene in strain DPD7001 was deleted.

A temperature-sensitive sacB plasmid, pTsCSE7.3 (U.S. Pat. No. 6,673,567), was used to construct a deletion of the lacI gene, encoding the Lac repressor, and the lacZYA operon. PCR primers were designed using the *E. coli* K12 genomic sequence for amplification of 1.0 kb regions flanking the lacIZYA region (Lac__1 primer, SEQ ID NO:27; Lac__2 primer, SEQ ID NO:28; Lac__3 primer, SEQ ID NO:29; Lac__4 primer, SEQ ID NO:30).

Each of the primers distal to the lacIZYA region contained an EagI site for cloning into pTsCSE7.3. Additionally, each of the primers proximal to the lac operon contained a complimentary 33 bp region used in a second PCR reaction. Primers Lac__1 and Lac__2 were used to generate a 1 kb PCR product with template DNA from *E. coli* K12 strain MG1655. Likewise, primers Lac__3 and Lac__4 were used to generate a 1 kb PCR product with template DNA from *E. coli* K12 strain MG1655. The products of these two PCR reactions were used as templates in a cross-over PCR reaction with Lac__1 and Lac__4 primers to generate a 2 kb region with a lacIZYA deletion. Following gel purification and EagI digestion, the cross over PCR product was successfully cloned into EagI-digested and CIP-treated pTsCSE7.3.

Electroporation was used to transform DPD7001 with four independent lacIZYA deletion plasmids. Selection for temperature-resistant, $Cm^R$ derivatives of DPD4119 or DPD7001 on LB plates containing 25 µg/ml chloramphenicol at 42° C. was conducted. One integrated plasmid in DPD7001 was isolated.

Figure 6:
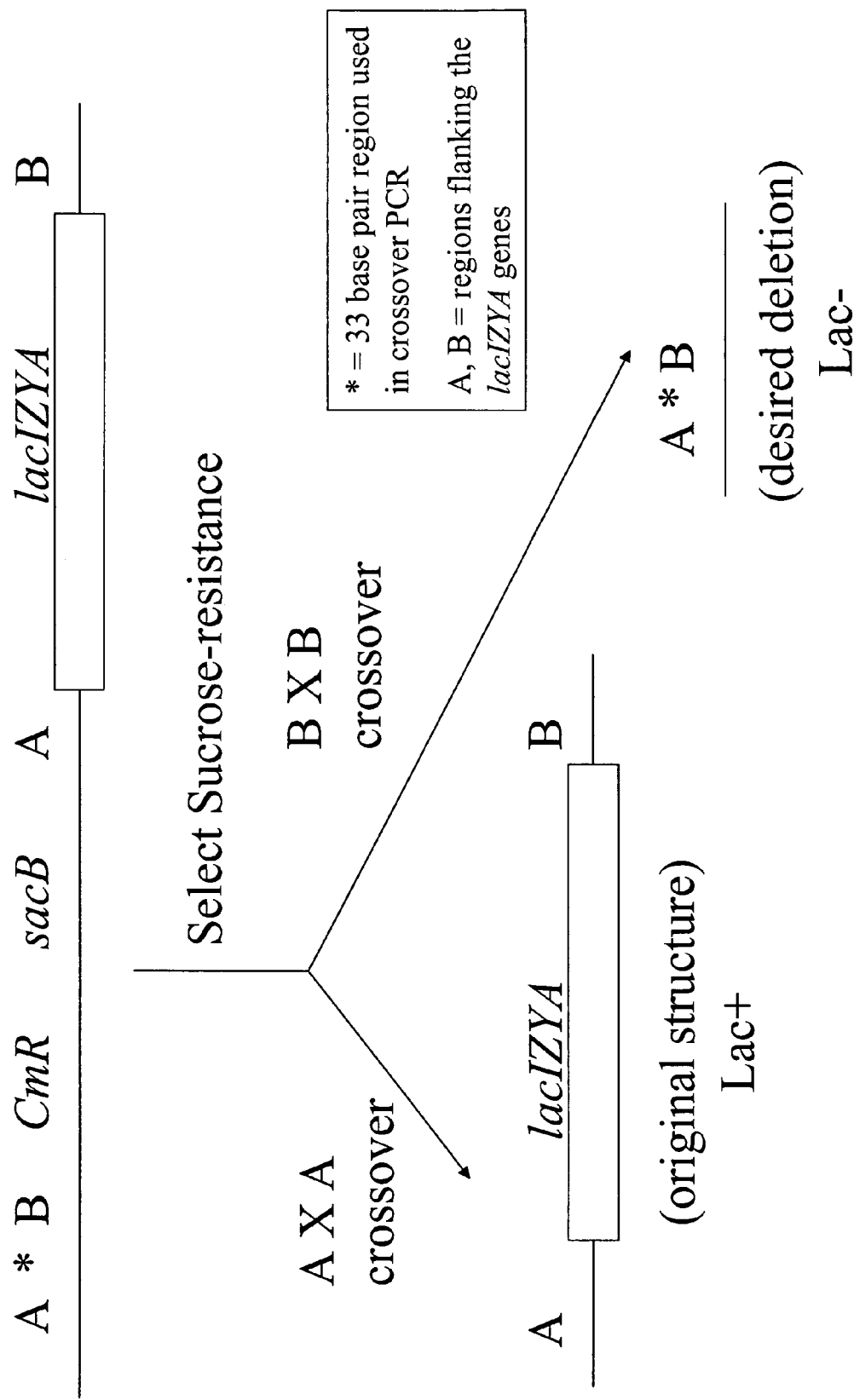
FIG. 6 shows two possible outcomes of sucrose resistance selection for a strain carrying an integrated sacB plasmid in the lacIZYA region.

This derivative of DPD7001 carrying the integrated deletion plasmid was subjected to sucrose counter-selection using LB plates carrying 5% sucrose at 42° C. This selection worked well, despite the fact that DPD7001 can utilize sucrose as a carbon source. As expected, both $Lac^+$ and $Lac^-$ strains were obtained from the sucrose resistance selection (see FIG. 6). The excision of the plasmid leading to the $Lac^+$ strains restores the original chromosomal structure. The crossover events resulting in the $Lac^-$ strains yield a deletion of lacIZYA and leave behind the 33 basepair segment, 5'-GT-TATAAATTTGGAGTGTGAAGGTTATTGCGTG-3', originally used to construct the deletion plasmid (see FIG. 6).

It was observed that both the $Lac^-$ and $Lac^+$ derivatives from the strain carrying the integrated plasmid in DPD7001 when streaked for single colonies on LB plates yielded small, like the parent, and medium sized colonies. Thus, five rounds of single colony purification on LB plates were conducted and the "small colony" or "medium colony" morphology was retained. PCR tests using primers outside the 2 kb lac operon flanking region verified the lac operon deletion in both the "small colony" and "medium colony" strains.

Several isolates were tested in duplicate for tyrosine and phenylalanine production in shake flasks using MOPS buffered medium with 2 g/l glucose and an initial 10 µg/ml phenylalanine (see Table 8 below).

TABLE 8

Tyrosine and phenylalanine excretion by different $Lac^-$ or $Lac^+$ strains

| Strain | Tyrosine ppm | Tyrosine, St Dev | Phe, ppm | Phe, St Dev | Final OD | Lac/colony size |
|---|---|---|---|---|---|---|
| DPD4145 | 359 | 1 | 82 | 3 | 1.12 | $Lac^-$ small |
| DPD4146 | 358 | 1 | 81 | 1 | 1.13 | $Lac^-$ small |
| DPD7001 | 289 | 12 | 110 | 2 | 1.2 | $Lac^+$ small |

TABLE 8-continued

Tyrosine and phenylalanine excretion by different $Lac^-$ or $Lac^+$ strains

| Strain | Tyrosine ppm | Tyrosine, St Dev | Phe, ppm | Phe, St Dev | Final OD | Lac/colony size |
|---|---|---|---|---|---|---|
| DPD4149 | 326 | 2 | 50 | 2 | 1.15 | $Lac^-$ medium |
| DPD4150 | 290 | 2 | 63 | 2 | 1.2 | $Lac^+$ medium |

The two "small colony" $Lac^-$ strains DPD4145 and DPD4146 had about 25% more tyrosine and 25% less phenylalanine than the parent strain, DPD7001. Thus, deletion of the gene for the LacI repressor apparently allows higher level expression of tyrA from the trc promoter. Hence the bottleneck at the chorismate->prephenate->phenylpyruvate steps catalyzed by the TyrA protein is partially relieved and greater amounts of tyrosine are excreted.

Example 8

Fermentation of Strain DPD4145 for Production of Tyrosine

Strain DPD4145, the construction of which is described in Example 7, was evaluated for production of tyrosine from glucose in a 10 L fermentation. The fermentation protocol and medium used were similar to those described in Example 6 except for the following notable differences. Unlike DPD4119, fermentation using DPD4145 was not induced with IPTG and no antibiotics were used during the entire protocol. Significant increase in tyrosine titer was achieved as shown in Table 9. Furthermore, lack of dependence on IPTG or antibiotics makes this strain amenable for economical scale-up.

TABLE 9

Strain DPD4145 fermentation for tyrosine production.

| Elapsed Fermentation Time (h) | L-Tyrosine (g/l) | L-Phenylalanine (g/l) | Biomass OD550 |
|---|---|---|---|
| 44 | 49.17 | 2.89 | 52.00 |
| 48 | 52.58 | 3.24 | 48.00 |
| 52 | 53.69 | 3.01 | 49.50 |
| 56 | 54.27 | 3.17 | 48.60 |

What is claimed is:

1. A method for making an L-tyrosine over-producing *E. coli* strain comprising:
   a) providing a strain of *E. coli*; and
   b) replacing the endogenous pheA-tyrA chromosomal region of the *E. coli* strain with an engineered chromosomal segment comprising a nucleic acid fragment comprising:
      1) a non-functional pheA coding region; and
      2) a wild type tyrA coding region operably linked to a promoter;
      wherein insertion of the engineered chromosomal segment generates the L-tyrosine over-producing *E. coli* strain.

2. The method according to claim 1, wherein the *E. coli* strain is selected from the group consisting of K12, O157:H7, and CFT073.

3. The method according to claim 2, wherein the *E. coli* strain is selected from the group consisting of ATCC #700926, ATCC #27325, ATCC #31882, ATCC #31884, and ATCC #13281.

4. The method according to claim 1, wherein the engineered chromosomal segment optionally comprises a selection marker.

5. The method according to claim 1, wherein the non-functional pheA nucleic acid sequence is a nucleic acid fragment comprising a deletion of at least a portion the pheA coding region.

6. The method according to claim 1, wherein the *E. coli* strain further comprises a mutation selected from the group consisting aroG397 and tyrR366.

7. The method according to claim 1, wherein the *E. coli* strain further comprises all of the following phenotypic traits:
   a) resistance to 3-fluorotyrosine;
   b) resistance to para-fluorophenylalanine; and
   c) resistance to beta-2-thienylalanine.

8. The method according to claim 1, wherein said promoter is selected from the group consisting of lac, ara, tet, trp, lambda $P_{L,\ lambda\ PR}$, T7, tac, trc, malE, T3, T4, T5, rrnB, lpp, phoA, proU, cst-1, cadA, nar, cspA, gyrA, *Bacillus* spp nprM, and *Streptomyces* spp glucose isomerase.

9. The method according to claim 1, wherein the L-tyrosine over-producing *E. coli* strain produces L-tyrosine at a concentration of at least 26 g/L.

* * * * *

SEQUENCE LISTING

<160> NUMBER OF SEQ ID NOS: 31

<210> SEQ ID NO 1
<211> LENGTH: 2551
<212> TYPE: DNA
<213> ORGANISM: Escherichia coli

<400> SEQUENCE: 1

```
aacgcgcctt cgggcgcgtt ttttgttgac agcgtgaaaa cagtacgggt actgtactaa      60
agtcacttaa ggaaacaaac atgaaacaca taccgttttt cttcgcattc tttttacct     120 tcccctgaat gggaggcgtt tcgtcgtgtg aaacagaatg cgaagacgaa caataaggcc    180
```

```
tcccaaatcg gggggccttt tttattgata acaaaaaggc aacactatga catcggaaaa    240
cccgttactg gcgctgcgag agaaaatcag cgcgctggat gaaaaattat tagcgttact    300
ggcagaacgg cgcgaactgg ccgtcgaggt gggaaaagcc aaactgctct cgcatcgccc    360
ggtacgtgat attgatcgtg aacgcgattt gctggaaaga ttaattacgc tcggtaaagc    420
gcaccatctg gacgcccatt acattactcg cctgttccag ctcatcattg aagattccgt    480
attaactcag caggctttgc tccaacaaca tctcaataaa attaatccgc actcagcacg    540
catcgctttt ctcggcccca aaggttctta ttcccatctt gcggcgcgcc agtatgctgc    600
ccgtcacttt gagcaattca ttgaaagtgg ctgcgccaaa tttgccgata tttttaatca    660
ggtggaaacc ggccaggccg actatgccgt cgtaccgatt gaaaatacca gctccggtgc    720
cataaacgac gtttacgatc tgctgcaaca taccagcttg tcgattgttg gcgagatgac    780
gttaactatc gaccattgtt tgttggtctc cggcactact gatttatcca ccatcaatac    840
ggtctacagc catccgcagc cattccagca atgcagcaaa ttccttaatc gttatccgca    900
ctggaagatt gaatataccg aaagtacgtc tgcggcaatg gaaaaggttg cacaggcaaa    960
atcaccgcat gttgctgcgt tgggaagcga agctggcggc actttgtacg gtttgcaggt   1020
actggagcgt attgaagcaa atcagcgaca aaacttcacc cgatttgtgg tgttggcgcg   1080
taaagccatt aacgtgtctg atcaggttcc ggcgaaaacc acgttgttaa tggcgaccgg   1140
gcaacaagcc ggtgcgctgg ttgaagcgtt gctggtactg cgcaaccaca atctgattat   1200
gacccgtctg gaatcacgcc cgattcacgg taatccatgg gaagagatgt tctatctgga   1260
tattcaggcc aatcttgaat cagcggaaat gcaaaaagca ttgaaagagt tagggaaat   1320 cacccgttca atgaaggtat tgggctgtta cccaagtgag aacgtagtgc ctgttgatcc   1380
aacctgatga aaaggtgccg gatgatgtga atcatccggc actggattat tactggcgat   1440
tgtcattcgc ctgacgcaat aacacgcggc tttcactctg aaaacgctgt gcgtaatcgc   1500
cgaaccagtg ctccaccttg cggaaactgt caataaacgc ctgcttatcg ccctgctcca   1560
gcaactcaat cgcctcgccg aaacgcttat agtaacgttt gattaacgcc agattacgct   1620
ctgacgacat aatgatgtcg gcataaagct gcggatcctg agcaaacagt cgcccgacca   1680
tcgccagctc aaggcggtaa atcggcgaag agagcgccag aagttgctca agctgaacat   1740
tttcttctgc caggtgcagc ccgtaagcaa aagtagcaaa gtggcgcagt gcctgaataa   1800
acgccatatt ctgatcgtgc tcgacggcgc taatacgatg cagccgagcg ccccagacct   1860
gaatttgctc cagaaaccat tggtatgctt ccggtttacg tccatcacac cagaccacaa   1920
cttgctttgc caggctaccg ctgtccggac cgaacatcgg gtgtagcccc agcaccggac   1980
catcatgcgc caccagcatg gcctgtaatg gcccattttt cactgatgcc agatcgacca   2040
gaatacaatc tttcggtaaa ggcggtaatt tgccaataac ttgctcagta acgtggattg   2100
gcacactaac aatcaccatt ccggcatcgg caacaatatc agccgctcga tcccagtcat   2160
gttgctccag aatccgcacc tgataacccg agagggtcag catcttctcg aacaggcgtc   2220
ccatctgacc gccaccgccg acgataacca ccggacgcag tgacggacaa agtgttttaa   2280
atcctttgtc gttttcactg gagtaagatt cacgcatcac ccgacgcaaa acatcctcaa   2340
tcagatctgg cggtacaccc agagcttccg cctctgcacg acgcgaggcc aacatagatg   2400
cctcgcgctc cggaacataa ataggcagtc aaagcggct tttcacctcg cccacttcag   2460
caaccagttc cagacgcttc gctaataaat tcagcagcgc tttatcgact tcatcaattt   2520
gatcgcgtaa tgcggtcaat tcagcaacca t                                  2551
```

<210> SEQ ID NO 2
<211> LENGTH: 2550
<212> TYPE: DNA
<213> ORGANISM: Escherichia coli

<400> SEQUENCE: 2

```
aacgcgcctt cgggcgcgtt ttttgttgac agcgtgaaaa cagtacgggt actgtactaa      60
agtcacttaa ggaaacaaac atgaaacaca caccgttttt cttcgcattc ttttttacct     120
tcccctgaat gggaggcgtt tcgtcgtgtg aaacagaatg cgaagaagaa caataaggcc     180
tcccaaatcg gggggccttt tttattgata acaaaaaggc aacactatga catcggaaaa     240
cccgttactg gcgctgcgag agaaaatcag cgcgctggat gaaaaattat tagcattact     300
ggcagagcgg cgcgaactgg ccgtcgaggt gggaaaagcc aaactgctct cgcatcgccc     360
ggtacgtgat attgatcgtg aacgcgattt actggaaaga ttaattacgc tcggtaaagc     420
gcaccatctg gacgcccatt acattactcg cctgttccag ctcatcattg aagattccgt     480
attaactcag caggctttgc tccaacaaca tctcaataaa attaatccgc actcagcacg     540
catcgctttt ctcggcccca aggttcttta ttcccatctt gcggcgcgcc agtatgctgc     600
ccgtcacttt gagcaattca ttgaaagtgg ctgcgccaaa tttgccgata tttttaatca     660
ggtggaaacc ggccaggccg actatgccgt cgtaccgatt gaaaatacca gctccggtgc     720
cataaatgac gtttacgatc tgctgcaaca taccagcttg tcgattgttg gcgagatgac     780
gttaactatc gaccattgtt tgttagtctc cggcacgact gatttatcca ccatcaatac     840
ggtctacagc catccgcagc cattccagca atgcagcaaa ttccttaatc gttatccgca     900
ctggaagatt gaatataccg aaagtacgtc tgcggcaatg gaaaaggttg cacaggcaaa     960
atcaccgcat gttgctgcgt taggaagcga agctggcggc actttgtacg gtttgcaggt    1020
actggagcgg attgaagcga atcagcgaca aaacttcacc cgatttgtgg tgttggcgcg    1080
taaagccatt aacgtgtctg atcaggttcc ggcgaaaacg acgttgttaa tggcgaccgg    1140
gcaacaagcc ggtgcgctgg ttgaagcgtt gctggtactg cgcaaccaca atctgattat    1200
gacccgtctg gaatcacgcc cgattcacgg taatccatgg gaagagatgt tttatctgga    1260
tattcaggcc aatcttgaat cagcggaaat gcaaaaagca ttgaaagagt taggggaaat    1320
cacccgttca atgaaggtat tgggctgtta ccctagtgag aacgtagtgc tgttgatcc    1380
aacctgatga aaggtgccg gatgatgtga atcatccggc actggattat tactggcgat    1440
tgtcattcgc ctgacgcaat aacacgcggc tttcactctg aaaacgctgt gcgtaatcgc    1500
cgaaccagtg ctccaccttg cggaaactgt caataaacgc ctgcttatcg ccctgctcca    1560
gcaactcaat cgcctcgccg aaacgcttat agtaacgttt gattaacgcc agattacgct    1620
ctgacgacat aataatgtcg gcataaagct gcggatcctg agcgaacagt cgcccgacca    1680
tcgccagctc aaggcggtaa atcggcgaag agagcgccag aagttgctca agctgaacat    1740
tttcttctgc caggtgcagc ccgtaagcaa aagtagcaaa gtggcgcagt gcctgaataa    1800
acgccatatt ctgatcgtgc tcgacggcgc taatacgatg caaccgagcg ccccagacct    1860
gaatttgctc cagaaaccat tggtatgctt ccggtttacg tccatcacac cagaccacaa    1920
cttgctttgc caggctaccg ctgtccggac cgaacattgg gtgtaacccc agtaccgggc    1980
catcgtgcgc cgccagcatg gcctgtaatg gtccattttt cactgatgcc agatcaacca    2040
gaatacaatc tttcggtaaa ggcggtaatt tgccaataac ttgctcagta acgtggattg    2100
gcacactaac aatcaccatt ccggcatcgg caacaatatc agccgctcga tcccagtcat    2160
```

-continued

| | |
|---|---|
| gttgctccag aatccgcacc tgataacccg agagtgtcag catcttctcg aacagacgtc | 2220 |
| ccatctgacc gccgccgcca acgataacta ccgggcgtaa cgcaggacaa agcgttttaa | 2280 |
| atcctttgtc gttttcactg gagtaagatt cacgcatcac ccgacgcaaa acatcctcaa | 2340 |
| tcagatctgg cggtacaccc agagcttccg cctctgcacg acgcgaggcc aacatagatg | 2400 |
| cctctcgctc cggaacataa ataggcagtc aaagcggct tttcacctcg cccacttcag | 2460 |
| caaccagttc cagacgcttc gctaataaat tcagcagcgc tttatcgact tcatcaattt | 2520 |
| gatcgcgtaa tgcggtcaat tcagcaacca | 2550 |

<210> SEQ ID NO 3
<211> LENGTH: 2550
<212> TYPE: DNA
<213> ORGANISM: Escherichia coli

<400> SEQUENCE: 3

| | |
|---|---|
| aacgcgcctt cgggcgcgtt ttttgttgac agcgtgaaaa cagtacgggt actgtactaa | 60 |
| agtcacttaa ggaaacaaac atgaaacaca caccgttttt cttcgcattc tttttttacct | 120 |
| tcccctgaat ggggaggcgtt tcgtcgtgtg aaacagaatg cgaagacgaa caataaggcc | 180 |
| tcccaaatcg gggggccttt tttattgata acaaaaaggc aacactatga catcggaaaa | 240 |
| cccgttactg cgcgctgcgag agaaaatcag cgcgctggat gaaaaattat tagcattact | 300 |
| ggcagagcga cgcgaactgg ccgtcgaggt gggaaaagcc aaactgctct cgcatcgccc | 360 |
| ggtacgtgat attgatcgtg aacgcgattt gctggaaaga ttaattacgc tcggtaaagc | 420 |
| gcaccatctg gacgcccatt acattactcg cctgttccag ctcatcattg aagattccgt | 480 |
| attaactcag caggctttgc tccagcaaca tctcaataaa attaatccgc actcagcacg | 540 |
| catcgctttt ctcggcccca aggttcttta ttcccatctt gcggcgcgcc agtatgctgc | 600 |
| tcgtcacttt gagcaattca ttgaaagtgg ctgcgccaaa tttgccgata tttttaatca | 660 |
| ggtggaaacc ggccaggccg actatgccgt cgtaccgatt gaaaatacca gctccggtgc | 720 |
| cataaacgac gtttacgatc tgctgcaaca taccagtttg tcgattgttg gcgagatgac | 780 |
| gttaactatc gatcattgtt tgttggtctc cggcactact gatttatccg ccatcaatac | 840 |
| ggtctacagc catccgcagc cattccagca atgcagcaaa ttccttaatc gttatccgca | 900 |
| ctggaagatt gaatataccg aaagtacgtc tgcggcaatg aaaaggttg cacaggcaaa | 960 |
| atcaccgcat gttgctgcgt tgggaagcga agctggcggc actttgtacg gtttgcaggt | 1020 |
| actggagcgt attgaagcga atcagcgaca aaacttcacc cgatttgtgg tgttggcacg | 1080 |
| taaagccatt aacgtttctg accaggttcc ggcgaaaacg acgttgttaa tggcgaccgg | 1140 |
| acaacaagct ggtgcactgg ttgaagcgtt gctggtactg cgcaatcaca gtctgattat | 1200 |
| gacccgtctg gaatcacgtc cgattcacgg taatccgtgg gaagagatgt tttatctgga | 1260 |
| tattcaggcc aatcttgaat cagcggaaat gcaaaaagca ttgaaagagt tagggaaat | 1320 |
| cacccgttcg atgaaggtat tgggctgtta cccaagtgag aacgtagtgc ctgttgatcc | 1380 |
| aacctgatga aaagtgccg gatgatgtga atcatccggc actggattat tactggcgat | 1440 |
| tgtcattcgc ctgacgcaat aacacgcggc tttcactctg aaaacgctgt gcgtaatcgc | 1500 |
| cgaaccagtg ctccaccttg cggaaactgt caataaacgc ctgcttatcg ccctgctcca | 1560 |
| gcagctcaat cgcctcgccg aaacgcttat agtaacgttt gattaacgcc agattacgct | 1620 |
| ctgacgacat aataatgtcg gcataaagct gcggatcctg agcaaacagt cgcccgacca | 1680 |

-continued

| | |
|---|---|
| tcgccagctc aaggcggtaa atcggcgaag agagcgccag tagttgctca agctgaacat | 1740 |
| tttcttctgc caggtgcagc ccataagcaa aagtagcaaa gtggcgcaga gcctgaataa | 1800 |
| acgccatatt ctgatcgtgc tcgacagcgc taatacgatg caaccgagcg ccccagacct | 1860 |
| gaatttgctc cagaaaccat tggtatgctt ccggcttacg tccatcacac cagaccacaa | 1920 |
| cttgctttgc caggctaccg ctgtccgggc cgaacatcgg gtgtaacccc agcaccgggc | 1980 |
| catcgtgcgc cgccagcatg gcctgtaatg gtccattttt caccgatgcc agatcaacca | 2040 |
| gaatacaatc tttcggtaaa ggcggtaatt tgccgataac ttgctcagta acgtggatgg | 2100 |
| gcacactaac aatcaccatt ccggcatcgg aaacaatatc agccgctcga tcccagtcat | 2160 |
| gttgctccag aatccgcacc tgataacccg agagtgtcag catcttctcg aacagacgtc | 2220 |
| ccatctgacc gccaccaccg acgataacca ccgggcgcag tgacggacaa agcgttttaa | 2280 |
| atcctttgtc gttttcactg gagtaagatt cacgcatcac ccgacgcaaa acatcctcaa | 2340 |
| tcagatctgg cggtacaccc agagcttccg cctctgcacg acgcgaggcc aacatagatg | 2400 |
| cctcgcgctc cggaacataa ataggcagtc caaagcggct tttcacctcg cccacttcag | 2460 |
| caaccagttc cagacgcttc gctaataaat tcagcagcgc tttatcgact tcatcaattt | 2520 |
| gatcgcgtaa tgcggtcaat tcagcaacca | 2550 |

<210> SEQ ID NO 4
<211> LENGTH: 1161
<212> TYPE: DNA
<213> ORGANISM: Escherichia coli

<400> SEQUENCE: 4

| | |
|---|---|
| atgacatcgg aaaacccgtt actggcgctg cgagagaaaa tcagcgcgct ggatgaaaaa | 60 |
| ttattagcgt tactggcaga acggcgcgaa ctggccgtcg aggtgggaaa agccaaactg | 120 |
| ctctcgcatc gcccggtacg tgatattgat cgtgaacgcg atttgctgga aagattaatt | 180 |
| acgctcggta aagcgcacca tctggacgcc cattacatta ctcgcctgtt ccagctcatc | 240 |
| attgaagatt ccgtattaac tcagcaggct ttgctccaac aacatctcaa taaaattaat | 300 |
| ccgcactcag cacgcatcgc ttttctcggc cccaaaggtt cttattccca tcttgcggcg | 360 |
| cgccagtatg ctgcccgtca ctttgagcaa ttcattgaaa gtggctgcgc caaatttgcc | 420 |
| gatatttta atcaggtgga aaccggccag gccgactatg ccgtcgtacc gattgaaaat | 480 |
| accagctccg gtgccataaa cgacgtttac gatctgctgc aacataccag cttgtcgatt | 540 |
| gttggcgaga tgacgttaac tatcgaccat tgtttgttgg tctccggcac tactgattta | 600 |
| tccaccatca atacggtcta cagccatccg cagccattcc agcaatgcag caaattcctt | 660 |
| aatcgttatc cgcactggaa gattgaatat accgaaagta cgtctgcggc aatggaaaag | 720 |
| gttgcacagg caaatcacc gcatgttgct gcgttgggaa gcgaagctgg cggcactttg | 780 |
| tacgtttgc aggtactgga gcgtattgaa gcaaatcagc gacaaaactt cacccgattt | 840 |
| gtggtgttgg cgcgtaaagc cattaacgtg tctgatcagg ttccggcgaa accacgttg | 900 |
| ttaatggcga ccgggcaaca agccggtgcg ctggttgaag cgttgctggt actgcgcaac | 960 |
| cacaatctga ttatgacccg tctggaatca cgcccgattc acggtaatcc atgggaagag | 1020 |
| atgttctatc tggatattca ggccaatctt gaatcagcgg aaatgcaaaa agcattgaaa | 1080 |
| gagttagggg aaatcacccg ttcaatgaag gtattgggct gttacccaag tgagaacgta | 1140 |
| gtgcctgttg atccaacctg a | 1161 |

<210> SEQ ID NO 5
<211> LENGTH: 1161
<212> TYPE: DNA
<213> ORGANISM: Escherichia coli

<400> SEQUENCE: 5

| | |
|---|---|
| atgacatcgg aaaacccgtt actggcgctg cgagagaaaa tcagcgcgct ggatgaaaaa | 60 |
| ttattagcat tactggcaga gcggcgcgaa ctggccgtcg aggtgggaaa agccaaactg | 120 |
| ctctcgcatc gcccggtacg tgatattgat cgtgaacgcg atttactgga aagattaatt | 180 |
| acgctcggta aagcgcacca tctggacgcc cattacatta ctcgcctgtt ccagctcatc | 240 |
| attgaagatt ccgtattaac tcagcaggct ttgctccaac aacatctcaa taaaattaat | 300 |
| ccgcactcag cacgcatcgc ttttctcggc cccaaaggtt cttattccca tcttgcggcg | 360 |
| cgccagtatg ctgcccgtca cttttgagcaa ttcattgaaa gtggctgcgc caaatttgcc | 420 |
| gatattttta atcaggtgga aaccggccag gccgactatg ccgtcgtacc gattgaaaat | 480 |
| accagctccg gtgccataaa tgacgtttac gatctgctgc aacataccag cttgtcgatt | 540 |
| gttggcgaga tgacgttaac tatcgaccat tgtttgttag tctccggcac gactgattta | 600 |
| tccaccatca atacggtcta cagccatccg cagccattcc agcaatgcag caaattcctt | 660 |
| aatcgttatc cgcactggaa gattgaatat accgaaagta cgtctgcggc aatggaaaag | 720 |
| gttgcacagg caaaatcacc gcatgttgct gcgttaggaa gcgaagctgg cggcactttg | 780 |
| tacggtttgc aggtactgga gcggattgaa gcgaatcagc gacaaaactt cacccgattt | 840 |
| gtggtgttgg cgcgtaaagc cattaacgtg tctgatcagg ttccggcgaa aacgacgttg | 900 |
| ttaatggcga ccgggcaaca agccggtgcg ctggttgaag cgttgctggt actgcgcaac | 960 |
| cacaatctga ttatgacccg tctggaatca cgcccgattc acggtaatcc atgggaagag | 1020 |
| atgttttatc tggatattca ggccaatctt gaatcagcgg aaatgcaaaa agcattgaaa | 1080 |
| gagttagggg aaatcacccg ttcaatgaag gtattgggct gttaccctag tgagaacgta | 1140 |
| gtgcctgttg atccaacctg a | 1161 |

<210> SEQ ID NO 6
<211> LENGTH: 1161
<212> TYPE: DNA
<213> ORGANISM: Escherichia coli

<400> SEQUENCE: 6

| | |
|---|---|
| atgacatcgg aaaacccgtt actggcgctg cgagagaaaa tcagcgcgct ggatgaaaaa | 60 |
| ttattagcat tactggcaga gcgacgcgaa ctggccgtcg aggtgggaaa agccaaactg | 120 |
| ctctcgcatc gcccggtacg tgatattgat cgtgaacgcg atttgctgga aagattaatt | 180 |
| acgctcggta aagcgcacca tctggacgcc cattacatta ctcgcctgtt ccagctcatc | 240 |
| attgaagatt ccgtattaac tcagcaggct ttgctccagc aacatctcaa taaaattaat | 300 |
| ccgcactcag cacgcatcgc ttttctcggc cccaaaggtt cttattccca tcttgcggcg | 360 |
| cgccagtatg ctgctcgtca cttttgagcaa ttcattgaaa gtggctgcgc caaatttgcc | 420 |
| gatattttta atcaggtgga aaccggccag gccgactatg ccgtcgtacc gattgaaaat | 480 |
| accagctccg gtgccataaa cgacgtttac gatctgctgc aacataccag tttgtcgatt | 540 |
| gttggcgaga tgacgttaac tatcgatcat tgtttgttgg tctccggcac tactgattta | 600 |
| tccgccatca atacggtcta cagccatccg cagccattcc agcaatgcag caaattcctt | 660 |
| aatcgttatc cgcactggaa gattgaatat accgaaagta cgtctgcggc aatggaaaag | 720 |

-continued

| | |
|---|---|
| gttgcacagg caaaatcacc gcatgttgct gcgttgggaa gcgaagctgg cggcactttg | 780 |
| tacggtttgc aggtactgga gcgtattgaa gcgaatcagc gacaaaactt cacccgattt | 840 |
| gtggtgttgg cacgtaaagc cattaacgtt tctgaccagg ttccggcgaa aacgacgttg | 900 |
| ttaatggcga ccggacaaca agctggtgca ctggttgaag cgttgctggt actgcgcaat | 960 |
| cacagtctga ttatgacccg tctggaatca cgtccgattc acggtaatcc gtgggaagag | 1020 |
| atgttttatc tggatattca ggccaatctt gaatcagcgg aaatgcaaaa agcattgaaa | 1080 |
| gagttagggg aaatcacccg ttcgatgaag gtattgggct gttacccaag tgagaacgta | 1140 |
| gtgcctgttg atccaacctg a | 1161 |

<210> SEQ ID NO 7
<211> LENGTH: 1122
<212> TYPE: DNA
<213> ORGANISM: Escherichia coli

<400> SEQUENCE: 7

| | |
|---|---|
| atggttgctg aattgaccgc attacgcgat caaattgatg aagtcgataa agcgctgctg | 60 |
| aatttattag cgaagcgtct ggaactggtt gctgaagtgg gcgaggtgaa aagccgcttt | 120 |
| ggactgccta tttatgttcc ggagcgcgag gcatctatgt tggcctcgcg tcgtgcagag | 180 |
| gcggaagctc tgggtgtacc gccagatctg attgaggatg ttttgcgtcg ggtgatgcgt | 240 |
| gaatcttact ccagtgaaaa cgacaaagga tttaaaacac tttgtccgtc actgcgtccg | 300 |
| gtggttatcg tcggcggtgg cggtcagatg ggacgcctgt tcgagaagat gctgacccta | 360 |
| tcgggttatc aggtgcggat tctggagcaa catgactggg atcgagcggc tgatattgtt | 420 |
| gccgatgccg gaatggtgat tgttagtgtg ccaatccacg ttactgagca agttattggc | 480 |
| aaattaccgc ctttaccgaa agattgtatt ctggtcgatc tggcatcagt gaaaaatggg | 540 |
| ccattacagg cctgctggt ggcgcatgat ggtccggtgc tggggctaca cccgatgttc | 600 |
| ggtccggaca gcggtagcct ggcaaagcaa gttgtggtct ggtgtgatgg acgtaaaccg | 660 |
| gaagcatacc aatggtttct ggagcaaatt caggtctggg gcgctcggct gcatcgtatt | 720 |
| agcgccgtcg agcacgatca gaatatggcg tttattcagg cactgcgcca ctttgctact | 780 |
| tttgcttacg ggctgcacct ggcagaagaa aatgttcagc ttgagcaact tctggcgctc | 840 |
| tcttcgccga tttaccgcct tgagctggcg atggtcgggc gactgtttgc tcaggatccg | 900 |
| cagctttatg ccgacatcat tatgtcgtca gagcgtaatc tggcgttaat caaacgttac | 960 |
| tataagcgtt tcggcgaggc gattgagttg ctggagcagg gcgataagca ggcgtttatt | 1020 |
| gacagtttcc gcaaggtgga gcactggttc ggcgattacg cacagcgttt tcagagtgaa | 1080 |
| agccgcgtgt tattgcgtca ggcgaatgac aatcgccagt aa | 1122 |

<210> SEQ ID NO 8
<211> LENGTH: 1122
<212> TYPE: DNA
<213> ORGANISM: Escherichia coli

<400> SEQUENCE: 8

| | |
|---|---|
| atggttgctg aattgaccgc attacgcgat caaattgatg aagtcgataa agcgctgctg | 60 |
| aatttattag cgaagcgtct ggaactggtt gctgaagtgg gcgaggtgaa aagccgcttt | 120 |
| ggactgccta tttatgttcc ggagcgagag gcatctatgt tggcctcgcg tcgtgcagag | 180 |
| gcggaagctc tgggtgtacc gccagatctg attgaggatg ttttgcgtcg ggtgatgcgt | 240 |
| gaatcttact ccagtgaaaa cgacaaagga tttaaaacgc tttgtcctgc gttacgcccg | 300 |

-continued

```
gtagttatcg ttggcggcgg cggtcagatg ggacgtctgt tcgagaagat gctgacactc      360
tcgggttatc aggtgcggat tctggagcaa catgactggg atcgagcggc tgatattgtt      420
gccgatgccg aatggtgat tgttagtgtg ccaatccacg ttactgagca agttattggc       480
aaattaccgc ctttaccgaa agattgtatt ctggttgatc tggcatcagt gaaaaatgga      540
ccattacagg ccatgctggc ggcgcacgat ggcccggtac tggggttaca cccaatgttc      600
ggtccggaca gcggtagcct ggcaaagcaa gttgtggtct ggtgtgatgg acgtaaaccg      660
gaagcatacc aatggtttct ggagcaaatt caggtctggg gcgctcggtt gcatcgtatt      720
agcgccgtcg agcacgatca gaatatggcg tttattcagg cactgcgcca ctttgctact      780
tttgcttacg gctgcacct ggcagaagaa aatgttcagc ttgagcaact tctggcgctc       840
tcttcgccga tttaccgcct tgagctgcg atggtcgggc gactgttcgc tcaggatccg        900
cagctttatg ccgacattat tatgtcgtca gagcgtaatc tggcgttaat caaacgttac      960
tataagcgtt tcggcgaggc gattgagttg ctggagcagg gcgataagca ggcgtttatt     1020
gacagtttcc gcaaggtgga gcactggttc ggcgattacg cacagcgttt tcagagtgaa     1080
agccgcgtgt tattgcgtca ggcgaatgac aatcgccagt aa                        1122
```

<210> SEQ ID NO 9
<211> LENGTH: 1122
<212> TYPE: DNA
<213> ORGANISM: Escherichia coli

<400> SEQUENCE: 9

```
atggttgctg aattgaccgc attacgcgat caaattgatg aagtcgataa agcgctgctg       60
aatttattag cgaagcgtct ggaactggtt gctgaagtgg gcgaggtgaa aagccgcttt      120
ggactgccta tttatgttcc ggagcgcgag gcatctatgt tggcctcgcg tcgtgcagag      180
gcggaagctc tgggtgtacc gccagatctg attgaggatg ttttgcgtcg ggtgatgcgt      240
gaatcttact ccagtgaaaa cgacaaagga tttaaaacgc tttgtccgtc actgcgcccg      300
gtggttatcg tcggtggtgg cggtcagatg ggacgtctgt tcgagaagat gctgacactc      360
tcgggttatc aggtgcggat tctggagcaa catgactggg atcgagcggc tgatattgtt      420
tccgatgccg aatggtgat tgttagtgtg cccatccacg ttactgagca agttatcggc       480
aaattaccgc ctttaccgaa agattgtatt ctggttgatc tggcatcggt gaaaaatgga      540
ccattacagg ccatgctggc ggcgcacgat ggcccggtgc tggggttaca cccgatgttc      600
ggcccggaca gcggtagcct ggcaaagcaa gttgtggtct ggtgtgatgg acgtaagccg      660
gaagcatacc aatggtttct ggagcaaatt caggtctggg gcgctcggtt gcatcgtatt      720
agcgctgtcg agcacgatca gaatatggcg tttattcagg ctctgcgcca ctttgctact      780
tttgcttatg gctgcacct ggcagaagaa aatgttcagc ttgagcaact actggcgctc      840
tcttcgccga tttaccgcct tgagctgcg atggtcgggc gactgtttgc tcaggatccg       900
cagctttatg ccgacattat tatgtcgtca gagcgtaatc tggcgttaat caaacgttac      960
tataagcgtt tcggcgaggc gattgagctg ctggagcagg gcgataagca ggcgtttatt     1020
gacagtttcc gcaaggtgga gcactggttc ggcgattacg cacagcgttt tcagagtgaa     1080
agccgcgtgt tattgcgtca ggcgaatgac aatcgccagt aa                        1122
```

<210> SEQ ID NO 10
<211> LENGTH: 385
<212> TYPE: PRT
<213> ORGANISM: Yersinia pestis

<400> SEQUENCE: 10

```
Met Thr Asp Asn Pro Leu Leu Val Leu Arg Glu Arg Ile Ser Ala Leu
1               5                   10                  15

Asp Leu Lys Leu Leu Ala Leu Leu Ala Glu Arg Arg Glu Leu Ala Val
            20                  25                  30

Asp Val Ala Lys Ala Lys Gln Leu His His Arg Pro Ile Arg Asp Lys
        35                  40                  45

Glu Arg Glu Arg Asp Leu Leu Asp Ala Leu Ile Asp Ala Ala Lys Pro
    50                  55                  60

Tyr Asn Leu Asp Gly Phe Tyr Val Thr Arg Leu Phe Gln Leu Ile Ile
65                  70                  75                  80

Glu Asp Ser Val Leu Thr Gln Gln Ala Leu Leu Gln His Gln Leu Asn
                85                  90                  95

Gln Thr Ala Leu Leu Ser Ala Arg Ile Ala Phe Leu Gly Pro Lys Gly
            100                 105                 110

Ser Tyr Ser His Leu Ala Ala Arg Gln Tyr Ala Ala Arg His Phe Glu
        115                 120                 125

Gln Leu Ile Glu Cys Gly Cys Leu Lys Phe Gln Asp Ile Phe Thr Gln
    130                 135                 140

Val Glu Thr Gly Gln Ala Asp Tyr Ala Val Leu Pro Ile Glu Asn Thr
145                 150                 155                 160

Ser Ser Gly Ser Ile Asn Asp Val Tyr Asp Leu Leu Gln His Thr Ser
                165                 170                 175

Leu Ser Ile Val Gly Glu Ile Thr Asn Pro Ile Glu His Cys Val Leu
            180                 185                 190

Ile Ala Thr Glu Thr Asp Leu Asn Lys Ile Glu Thr Val Tyr Ser His
        195                 200                 205

Pro Gln Pro Phe Gln Gln Cys Ser Gln Phe Ile Asn Arg Phe Pro His
    210                 215                 220

Trp Lys Ile Glu Tyr Cys Glu Ser Thr Ala Ala Ala Met Glu Lys Val
225                 230                 235                 240

Ala Gly Met Lys Ser Pro Thr Ala Ala Leu Gly Ser Glu Ala Gly Gly
                245                 250                 255

Gly Ala Leu Tyr Asn Leu Gln Val Leu Glu His Asn Leu Ala Asn Gln
            260                 265                 270

Gln Gln Asn Ile Thr Arg Phe Ile Val Leu Ala Arg Lys Pro Ile Asp
        275                 280                 285

Val Ser Glu Gln Ile Pro Ala Lys Thr Thr Leu Ile Met Ala Thr Gly
290                 295                 300

Gln Gln Ser Gly Ala Leu Val Glu Ala Leu Leu Val Leu Arg Glu His
305                 310                 315                 320

Gly Ile Ile Met Thr Lys Leu Glu Ser Arg Pro Ile Asn Gly Asn Pro
                325                 330                 335

Trp Glu Glu Met Phe Tyr Ile Asp Val Gln Ala Asn Ile Arg Ser Glu
            340                 345                 350

Ala Met Gln Lys Ala Leu Ala Asp Leu Thr Pro Ile Thr Arg Ser Leu
        355                 360                 365

Lys Val Leu Gly Cys Tyr Pro Ser Glu Asn Val Val Pro Val Glu Pro
    370                 375                 380

Arg
385
```

<210> SEQ ID NO 11
<211> LENGTH: 386
<212> TYPE: PRT
<213> ORGANISM: Escherichia coli

<400> SEQUENCE: 11

```
Met Thr Ser Glu Asn Pro Leu Leu Ala Leu Arg Glu Lys Ile Ser Ala
1               5                   10                  15

Leu Asp Glu Lys Leu Leu Ala Leu Leu Ala Glu Arg Arg Glu Leu Ala
            20                  25                  30

Val Glu Val Gly Lys Ala Lys Leu Leu Ser His Arg Pro Val Arg Asp
        35                  40                  45

Ile Asp Arg Glu Arg Asp Leu Leu Glu Arg Leu Ile Thr Leu Gly Lys
    50                  55                  60

Ala His His Leu Asp Ala His Tyr Ile Thr Arg Leu Phe Gln Leu Ile
65                  70                  75                  80

Ile Glu Asp Ser Val Leu Thr Gln Gln Ala Leu Leu Gln Gln His Leu
                85                  90                  95

Asn Lys Ile Asn Pro His Ser Ala Arg Ile Ala Phe Leu Gly Pro Lys
            100                 105                 110

Gly Ser Tyr Ser His Leu Ala Ala Arg Gln Tyr Ala Ala Arg His Phe
        115                 120                 125

Glu Gln Phe Ile Glu Ser Gly Cys Ala Lys Phe Ala Asp Ile Phe Asn
    130                 135                 140

Gln Val Glu Thr Gly Gln Ala Asp Tyr Ala Val Val Pro Ile Glu Asn
145                 150                 155                 160

Thr Ser Ser Gly Ala Ile Asn Asp Val Tyr Asp Leu Leu Gln His Thr
                165                 170                 175

Ser Leu Ser Ile Val Gly Glu Met Thr Leu Thr Ile Asp His Cys Leu
            180                 185                 190

Leu Val Ser Gly Thr Thr Asp Leu Ser Thr Ile Asn Thr Val Tyr Ser
        195                 200                 205

His Pro Gln Pro Phe Gln Gln Cys Ser Lys Phe Leu Asn Arg Tyr Pro
    210                 215                 220

His Trp Lys Ile Glu Tyr Thr Glu Ser Thr Ser Ala Ala Met Glu Lys
225                 230                 235                 240

Val Ala Gln Ala Lys Ser Pro His Val Ala Ala Leu Gly Ser Glu Ala
                245                 250                 255

Gly Gly Thr Leu Tyr Gly Leu Gln Val Leu Glu Arg Ile Glu Ala Asn
            260                 265                 270

Gln Arg Gln Asn Phe Thr Arg Phe Val Val Leu Ala Arg Lys Ala Ile
        275                 280                 285

Asn Val Ser Asp Gln Val Pro Ala Lys Thr Thr Leu Leu Met Ala Thr
    290                 295                 300

Gly Gln Gln Ala Gly Ala Leu Val Glu Ala Leu Leu Val Leu Arg Asn
305                 310                 315                 320

His Asn Leu Ile Met Thr Arg Leu Glu Ser Arg Pro Ile His Gly Asn
                325                 330                 335

Pro Trp Glu Glu Met Phe Tyr Leu Asp Ile Gln Ala Asn Leu Glu Ser
            340                 345                 350

Ala Glu Met Gln Lys Ala Leu Lys Glu Leu Gly Glu Ile Thr Arg Ser
        355                 360                 365
```

```
Met Lys Val Leu Gly Cys Tyr Pro Ser Glu Asn Val Val Pro Val Asp
        370                 375                 380

Pro Thr
385

<210> SEQ ID NO 12
<211> LENGTH: 386
<212> TYPE: PRT
<213> ORGANISM: Erwinia carotovora

<400> SEQUENCE: 12

Met Thr Asp Asn Pro Leu Leu Val Leu Arg Glu Arg Ile Ser Ala Leu
1               5                   10                  15

Asp Leu Gln Leu Ile Glu Leu Leu Ala Gln Arg Arg Glu Leu Ala Leu
            20                  25                  30

Gly Val Ala Arg Ser Lys Leu His Ser His Arg Pro Ile Arg Asp Lys
        35                  40                  45

Glu Arg Glu Arg Asp Leu Leu Asp Lys Leu Thr Ala Ala Gly Lys Lys
    50                  55                  60

His His Leu Asp Gly His Tyr Ile Thr Arg Leu Phe Gln Leu Ile Ile
65                  70                  75                  80

Glu Asp Ser Val Leu Thr Gln Gln Ala Leu Leu Gln His His Leu Asn
                85                  90                  95

Gln Thr Thr Ser His Ser Ala Arg Val Ala Phe Leu Gly Pro Lys Gly
            100                 105                 110

Ser Tyr Ser His Leu Ala Ala Arg Gln Tyr Ser Ala Arg His Phe Glu
        115                 120                 125

Gln Phe Ile Glu Cys Gly Cys Gln Lys Phe Gln Asp Ile Phe Asn Met
    130                 135                 140

Val Glu Thr Gly Gln Ala Asp Tyr Ala Val Leu Pro Ile Glu Asn Thr
145                 150                 155                 160

Ser Ser Gly Ser Ile Asn Asp Val Tyr Asp Leu Leu Gln His Thr Ser
                165                 170                 175

Leu Ser Ile Val Gly Glu Leu Thr Asn Pro Ile Asn His Cys Val Leu
            180                 185                 190

Val Ala Thr Asp Thr Ser Leu Ala Gln Ile Glu Thr Val Tyr Ser His
        195                 200                 205

Pro Gln Pro Phe Gln Gln Cys Ser His Phe Ile Asn Arg Phe Pro His
    210                 215                 220

Trp Lys Ile Glu Tyr Cys Glu Ser Thr Ala Ala Ala Met Glu Lys Val
225                 230                 235                 240

Ala Ala Leu Asn Ser Pro Lys Ala Ala Ala Leu Gly Ser Glu Ala Gly
                245                 250                 255

Gly Gln Leu Tyr Gln Leu Gln Met Leu Glu His Asn Leu Ala Asn Gln
            260                 265                 270

Ser Gln Asn Ile Thr Arg Phe Ile Val Leu Ala Arg Lys Pro Ile Asp
        275                 280                 285

Val Thr Glu Gln Val Pro Ala Lys Thr Thr Leu Ile Met Ala Thr Gly
    290                 295                 300

Gln Gln Ser Gly Ala Leu Val Glu Ala Leu Leu Val Leu Arg Asp Asn
305                 310                 315                 320

Gly Ile Val Met Thr Lys Leu Glu Ser Arg Pro Ile Asn Gly Asn Pro
                325                 330                 335

Trp Glu Glu Met Phe Tyr Leu Asp Val Gln Ala Asn Leu Arg Gly Asp
            340                 345                 350
```

-continued

```
Ala Met Gln Lys Ala Leu Lys Gly Leu Ala Pro Ile Thr Arg Ser Leu
            355                 360                 365

Lys Val Leu Gly Cys Tyr Pro Ser Glu Asn Val Val Pro Val Asp Val
        370                 375                 380

Asn Glu
385
```

<210> SEQ ID NO 13
<211> LENGTH: 1122
<212> TYPE: DNA
<213> ORGANISM: Salmonella typhimurium

<400> SEQUENCE: 13

```
atggttgctg aattgaccgc attacgcgat caaatagatg atgtcgataa agcgttgttg      60
aatttactgg ctaagcgcct ggaactggtt gccaaagtcg gcgaggtgaa aagccgtttt    120
ggcctgccta tttacgtgcc ggagcgtgag gcctctatgc tggcttcacg acgggcggaa    180
gcagaagcga tcggtgtccc gcccgatctc attgaagatg tcctgcgccg ggtaatgcgt    240
gaatcttact ccagcgaaaa tgataagggg ttcaaaacgc tttgtccttc tctgcgtccg    300
gtcgtcattg tgggcggcgg cggacagatg gggcgtctgt ttgaaaaaat gctcacgctg    360
tcgggctatc aggtccgtat tctggaacag caggactggc cgcgcgccag ggacattgtc    420
gccgatgccg gaatggtgat cgtcagcgtg ccgattcatg ttactgaaca ggtcatagcg    480
caactgccgc ccctgccgtc cgactgtatt ctggtcgatc tggcatcggt gaaaagcggt    540
ccgttgcagg caatgttggc ggcccatgat ggccccgtgt gggcttgca tccgatgttt    600
ggtccggaca gcgggagcct ggcgaagcag gtggtggtct ggtgtgacgg cgtcaaccg    660
gaagcgtatc agtggttcct tgagcaaatc caggtgtggg cgcgcggtt gcatcgaatt    720
agcgctgtcg agcacgatca gaacatggct tttatccagg cgttgcgcca ctttgctacc    780
ttcgcttatg gctgcatct ggcggaagag aacgtccagc ttgagcagct tctggcgcta    840
tcatcgccga tttatcgact ggagctggcg atggtcgggc gtctgttcgc ccaggacccg    900
caactgtatg cggacattat tatgtcgtcg gagcgcaatc tggcgcttat caagcgttac    960
tataaacgtt ttggcgatgc gatcgggtta ctggaacagg gtgataagca ggcttttatc   1020
gacagtttc gcaaagttga acactggttt ggcgattatg ccagacgctt ccagaatgaa   1080
agccgtgtgt tattgcgtca ggcgaatgac agccgaccat aa                       1122
```

<210> SEQ ID NO 14
<211> LENGTH: 1122
<212> TYPE: DNA
<213> ORGANISM: Photorhabdus luminescens

<400> SEQUENCE: 14

```
atggcggctg aattatctca attgcgggat aagattgatg aagtggataa agctttgctg      60
ggcttgctgg caaagcgtct ggaattggtt gcagagattg tgaggtaaa aagtcagaat    120
gggctgtcaa tttatgcacc tgacagagaa atggcgatgc ttgcttcacg tcggcaggag    180
gccgaagagt ttggtgttcc accggattta attgaggata ttctgcgccg cattatgcgg    240
gagtcttata ccagtgagaa taacaagggg tttaaaacgc tttgccctca attggggccg    300
atagtcattg ttggtggctt gggcaaaatg gggaaactat ttggccgttt gttaactttg    360
tctggttatg aagtcagaaa tctggaacca caagattggc ctaacgcgga acaaattctg    420
gcgggagtgg ggatggtgat tatcagtgta cctattcatt tgacagaaga agttattcgc    480
```

-continued

| | |
|---|---|
| cgtttaccgc cattacctga ccattgcatt ttggtggact tagcgtccgt taaacagcag | 540 |
| ccattacagg ctatgcttga tgtgcataaa ggtccagtgt tgggattaca tcctatgttt | 600 |
| gggccggatg tcggtagttt ggtaaaacaa gttgttgttt actgtgacgg acgtcaagag | 660 |
| gaagcttatc aatggttttt agaacagttg ttaatttggg gggcttgctt gcatcaaatg | 720 |
| agccctgaac agcatgataa aaacatgagc tttattcagg cgttgcgcca tttcacgaca | 780 |
| tttgcttatg ggcaacatct cgcacaggaa ggggcggatt acaacaact gttatcaata | 840 |
| tcttcaccta tttaccgttt ggaattgatc atggtcgggc gcttatttgc gcaagatccc | 900 |
| cagctctacg cggatattat tatgtcatca ccagagaata ttgatcttat acgccgttat | 960 |
| catcaaagtt ttggacaagc gttagagata ttggaaagcc aggacaaacg ggcttttgtc | 1020 |
| agcagttttg aagatgttag tgaatggttt ggtgattatg cacctcgttt tatgagggaa | 1080 |
| agcagggtat tgcttcaaca agcgaatgat agtcgccaat aa | 1122 |

<210> SEQ ID NO 15
<211> LENGTH: 1140
<212> TYPE: DNA
<213> ORGANISM: Shewanella sp.

<400> SEQUENCE: 15

| | |
|---|---|
| atgaatgaaa aaccacatc cgaattagaa catcttcgag gactgatcga cggtgtcgat | 60 |
| cagcaattgc tgcatttact gcgtaaacgc ttagatttag tcgcccaagt cggcacggta | 120 |
| aagcacgctg caggattacc catttatgca ccacagcgtg aagcggcaat gctggcaaaa | 180 |
| cgccgtgaag aagcccaaac catgggcatt gcgccacaat tgattgaaga tattttacgt | 240 |
| cgcctaatgc gtgaatccta tcttaatgaa aaggatgttg gctttaagca agtcaagaat | 300 |
| gatttaggtt cggtagttat agtgggcggt aaaggccagc ttggcgggct gtttcaacaa | 360 |
| atgctgagac tgtcaggtta tcaagtgaaa gtgctcgata agatgattg caacaagcg | 420 |
| gaatgcttat ttgccgatgc tggattggta ttagtgacag tgcctattgc catcacctgc | 480 |
| gacattatcc gtgaaaagct aactcagtta ccacgggact gtattctagc cgatttaacc | 540 |
| tccatcaaga cggaacccat gcaggcgatg ttggccgctc ataaggggcc tgttgtcggc | 600 |
| tttcatccga tgtttggtcc agatgtcggt agcttagcta agcaggttgt ggtggtgtgt | 660 |
| catgggcgcg aagctgataa ataccaatgg ttactcgaac aaattgccat tggggcgca | 720 |
| cggattgtcg aagctgagcc tgaatgtcac gataatgcga tgcaactggt gcaggcgatg | 780 |
| cgccatttct caacctttgt ctatggctta atctttgca aagaagaggc ggatatagag | 840 |
| actttattga aatttagctc gccaatctac cgcttagagt tagcgatggt gggccgttta | 900 |
| tttgcccaaa gcccggagct ttacgctgat attattttg ctcagcagga gagccagcat | 960 |
| gcgattggcg attatctgga taactatcgc gaagccttag aattgctgaa acggggcgat | 1020 |
| agagaggagt ttatcaatca gttccaaatg gttgccaagt ggtttggtga ttttgcaccg | 1080 |
| cagtttcagc gcgaaagtcg catgatgctg caatcggtaa gtgatatgaa acgaactga | 1140 |

<210> SEQ ID NO 16
<211> LENGTH: 1128
<212> TYPE: DNA
<213> ORGANISM: Xanthomonas campestris

<400> SEQUENCE: 16

| | |
|---|---|
| gtgatcgcgc atccggtcgt tggcatcgtc gggatcgccg cgcctacgg acgctggctc | 60 |
| gcccaattcc tgcgcacgcg catggggctg gaggtgatcg gcgtggatcc ggcattaccg | 120 |

```
gacgggctgg acgacgccac gctggtggcg cgcgccgatg tgctgatttt ttcggcacca      180
atccgccaca ccgctgcgct gatcgaacgc tatgccgctc ttgccggcgc gcgtgcggcg      240
gagcaactgt ggctggatgt cacctcgatc aaacaggcgc cagtcgcggc gatgctggcg      300
tcgcaggccg aggtggtggg cctgcacccg atgaccgcac cgcccaagtc gcccaccttg      360
aaggggcggg tgatggtggt ctgccgcgca cgtgtgcagc gctggtccgg ctgggtggat      420
gcgctgtgca gcgcgttgca ggccgagtgc gtctacgcca cgcccgaaca ccacgaccgc      480
gtgatggcgc tcgtgcaggc catggtgcat gccacccatc tggcgcaggc tggcaccttg      540
cgcgactacg ccccccttgct cggcgagttg cgcaccttga tgccataccg ctcggcctcg      600
ttcgaactgg ataccgcggt gatcgcgcgc attctctcgc tcaacccgtc gatctacgaa      660
gacatccagt tcggcaatcc ttacgttgcc gaaatgctcg accgcttgct cgcgcagctg      720
caagaactgc gcggcttggt ggtgcagggc gatgatgcgg cacgcttgcg atttcggcag      780
gcctttctcg atgccaacgc gcaggccctg caaggcgact cactggcggc cggcaactac      840
acctatgaac gggtgggcta cctgctggcc gacctcaccg agccgctgac cttgagcgtg      900
tatctgcccg aagaccagcc gggctcgtta cgcgtgttgc tgcatgtatt cgagcagcac      960
ggcgtcaacc tgtcctcgat ccactcctcg cgcacgcccg gcggcgagct gcacttccgg      1020
atggggttcg agccggagag cgatcgcgct gcactgggcc gcgccgcagc gcaaatcgat      1080
gccgaccgga tcgggcgggt gttggagcgc gttgatcggg aacgttga                  1128

<210> SEQ ID NO 17
<211> LENGTH: 140
<212> TYPE: DNA
<213> ORGANISM: Artificial
<220> FEATURE:
<223> OTHER INFORMATION: primer ABTR

<400> SEQUENCE: 17
tgaagaagag tagtcctttta tattgagtgt atcgccaacg cgccttcggg cgcgtttttt      60
tgaaaaggtg ccggatgatg tgaatcatcc ggcactggat tattactggc gattgtcatt      120
ttaagaccca ctttcacatt                                                  140

<210> SEQ ID NO 18
<211> LENGTH: 140
<212> TYPE: DNA
<213> ORGANISM: Artificial
<220> FEATURE:
<223> OTHER INFORMATION: primer BATA

<400> SEQUENCE: 18
aatgacaatc gccagtaata atccagtgcc ggatgattca catcatccgg cacctttttca     60 aaaaaacgcg cccgaaggcg cgttggcgat acactcaata taaggacta ctcttcttca      120 ctaagcactt gtctcctgtt                                                  140

<210> SEQ ID NO 19
<211> LENGTH: 20
<212> TYPE: DNA
<213> ORGANISM: Artificial
<220> FEATURE:
<223> OTHER INFORMATION: primer TR

<400> SEQUENCE: 19
ttaagaccca ctttcacatt                                                  20
```

```
<210> SEQ ID NO 20
<211> LENGTH: 20
<212> TYPE: DNA
<213> ORGANISM: Artificial
<220> FEATURE:
<223> OTHER INFORMATION: primer TA

<400> SEQUENCE: 20
ctaagcactt gtctcctgtt                                              20

<210> SEQ ID NO 21
<211> LENGTH: 66
<212> TYPE: DNA
<213> ORGANISM: Artificial
<220> FEATURE:
<223> OTHER INFORMATION: primer T-kan(tyrA)

<400> SEQUENCE: 21
aattcatcag gatctgaacg ggcagctgac ggctcgcgtg gcttaacgtc ttgagcgatt   60
gtgtag                                                             66

<210> SEQ ID NO 22
<211> LENGTH: 64
<212> TYPE: DNA
<213> ORGANISM: Artificial
<220> FEATURE:
<223> OTHER INFORMATION: primer B-kan(trc)

<400> SEQUENCE: 22
aaaacattat ccagaacggg agtgcgcctt gagcgacacg aatatgaata tcctccttag   60
ttcc                                                               64

<210> SEQ ID NO 23
<211> LENGTH: 40
<212> TYPE: DNA
<213> ORGANISM: Artificial
<220> FEATURE:
<223> OTHER INFORMATION: primer T-trc(kan)

<400> SEQUENCE: 23
ctaaggagga tattcatatt cgtgtcgctc aaggcgcact                        40

<210> SEQ ID NO 24
<211> LENGTH: 66
<212> TYPE: DNA
<213> ORGANISM: Artificial
<220> FEATURE:
<223> OTHER INFORMATION: primer B-trc(tyrA)

<400> SEQUENCE: 24
cgacttcatc aatttgatcg cgtaatgcgg tcaattcagc aaccatggtc tgtttcctgt   60
gtgaaa                                                             66

<210> SEQ ID NO 25
<211> LENGTH: 26
<212> TYPE: DNA
<213> ORGANISM: Artificial
<220> FEATURE:
<223> OTHER INFORMATION: primer T-ty(test)

<400> SEQUENCE: 25
caaccgcgca gtgaaatgaa atacgg                                       26
```

<210> SEQ ID NO 26
<211> LENGTH: 26
<212> TYPE: DNA
<213> ORGANISM: Artificial
<220> FEATURE:
<223> OTHER INFORMATION: primer B-ty(test)

<400> SEQUENCE: 26
gcgctccgga acataaatag gcagtc                                          26

<210> SEQ ID NO 27
<211> LENGTH: 32
<212> TYPE: DNA
<213> ORGANISM: Artificial
<220> FEATURE:
<223> OTHER INFORMATION: Lac_1 primer

<400> SEQUENCE: 27
gttagccggc cgtggggtgg ggatcggcat ca                                   32

<210> SEQ ID NO 28
<211> LENGTH: 53
<212> TYPE: DNA
<213> ORGANISM: Artificial
<220> FEATURE:
<223> OTHER INFORMATION: Lac_2 primer

<400> SEQUENCE: 28
cacgcaataa ccttcacact ccaaatttat aactatttca aagattataa agt            53

<210> SEQ ID NO 29
<211> LENGTH: 53
<212> TYPE: DNA
<213> ORGANISM: Artificial
<220> FEATURE:
<223> OTHER INFORMATION: Lac_3 primer

<400> SEQUENCE: 29
gttataaatt tggagtgtga aggttattgc gtgataacgt tactggtttc aca            53

<210> SEQ ID NO 30
<211> LENGTH: 32
<212> TYPE: DNA
<213> ORGANISM: Artificial
<220> FEATURE:
<223> OTHER INFORMATION: Lac_4 primer

<400> SEQUENCE: 30
agcagtcggc cgctacaatc aaaacatgcc cg                                   32

<210> SEQ ID NO 31
<211> LENGTH: 1542
<212> TYPE: DNA
<213> ORGANISM: Escherichia coli

<400> SEQUENCE: 31
atgcgtctgg aagtcttttg tgaagaccga ctcggtctga cccgcgaatt actcgatcta     60
ctcgtgctaa gaggcattga tttacgcggt attgagattg atcccattgg gcgaatctac    120
ctcaattttg ctgaactgga gtttgagagt tcagcagtc tgatggccga aatacgccgt    180
attgcgggtg ttaccgatgt gcgtactgtc ccgtggatgc cttccgaacg tgagcatctg    240
gcgttgagcg cgttactgga ggcgttgcct gaacctgtgc tctctgtcga tatgaaaagc    300
aaagtggata tggcgaaccc ggcgagctgt cagcttttg ggcaaaaatt ggatcgcctg    360

-continued

```
cgcaaccata ccgccgcaca attgattaac ggctttaatt ttttacgttg gctggaaagc    420
gaaccgcaag attcgcataa cgagcatgtc gttattaatg ggcagaattt cctgatggag    480
attacgcctg tttatcttca ggatgaaaat gatcaacacg tcctgaccgg tgcggtggtg    540
atgttgcgat caacgattcg tatgggccgc cagttgcaaa atgtcgccgc ccaggacgtc    600
agcgccttca gtcaaattgt cgccgtcagc ccgaaaatga agcatgttgt cgaacaggcg    660
cagaaactgg cgatgctaag cgcgccgctg ctgattacgg gtgacacagg tacaggtaaa    720
gatctctttg cctacgcctg ccatcaggca agcccagag cgggcaaacc ttacctggcg    780
ctgaactgtg cgtctatacc ggaagatgcg gtcgagagtg aactgtttgg tcatgctccg    840
gaagggaaga aaggattctt tgagcaggcg aacggtggtt cggtgctgtt ggatgaaata    900
ggggaaatgt caccacggat gcaggcgaaa ttactgcgtt tccttaatga tggcacttc    960
cgtcgggttg gcgaagacca tgaggtgcat gtcgatgtgc gggtgatttg cgctacgcag   1020
aagaatctgg tcgaactggt gcaaaaaggc atgttccgtg aagatctcta ttatcgtctg   1080
aacgtgttga cgctcaatct gccgccgcta cgtgactgtc cgcaggacat catgccgtta   1140
actgagctgt tcgtcgcccg ctttgccgac gagcagggcg tgccgcgtcc gaaactggcc   1200
gctgacctga atactgtact tacgcgttat gcgtggccgg gaaatgtgcg gcagttaaag   1260
aacgctatct atcgcgcact gacacaactg gacggttatg agctgcgtcc acaggatatt   1320
ttgttgccgg attatgacgc cgcaacggta gccgtgggcg aagatgcgat ggaaggttcg   1380
ctggacgaaa tcaccagccg ttttgaacgc tcggtattaa cccagcttta tcgcaattat   1440
cccagcacgc gcaaactggc aaaacgtctc ggcgtttcac ataccgcgat tgccaataag   1500
ttgcgggaat atggtctgag tcagaagaag aacgaagagt aa                      1542
```